US011832855B2

(12) United States Patent
Lee et al.

(10) Patent No.: US 11,832,855 B2
(45) Date of Patent: Dec. 5, 2023

(54) UNILATERAL IMPLANT HOLDERS AND RELATED METHODS

(71) Applicant: Medos International Sarl, Le Locle (CH)

(72) Inventors: Kevin Lee, Canton, MA (US); Mark Hall, Bridgewater, MA (US)

(73) Assignee: Medos International Sårl, Le Locle (CH)

( * ) Notice: Subject to any disclaimer, the term of this patent is extended or adjusted under 35 U.S.C. 154(b) by 317 days.

(21) Appl. No.: 17/187,716

(22) Filed: Feb. 26, 2021

(65) Prior Publication Data

US 2021/0177469 A1    Jun. 17, 2021

Related U.S. Application Data

(63) Continuation of application No. 15/843,618, filed on Dec. 15, 2017, now Pat. No. 10,966,762.

(51) Int. Cl.
*A61B 17/70* (2006.01)
*A61B 17/00* (2006.01)

(52) U.S. Cl.
CPC ...... *A61B 17/7083* (2013.01); *A61B 17/7032* (2013.01); *A61B 17/7074* (2013.01);
(Continued)

(58) Field of Classification Search
CPC ............ A61B 17/7085; A61B 17/7032; A61B 17/7091; A61B 17/7076; A61B 17/7083;
(Continued)

(56) References Cited

U.S. PATENT DOCUMENTS

| 410,780 A | 9/1889 | Cahn |
|---|---|---|
| 1,470,313 A | 10/1923 | Woolen |

(Continued)

FOREIGN PATENT DOCUMENTS

| CN | 102488548 B | 9/2013 |
|---|---|---|
| DE | 4238339 A1 | 5/1994 |

(Continued)

OTHER PUBLICATIONS

U.S. Appl. No. 15/843,618, filed Dec. 15 2017, Unilateral Implant Holders and Related Methods.
(Continued)

*Primary Examiner* — Eduardo C Robert
*Assistant Examiner* — Tara Rose E Carter
(74) *Attorney, Agent, or Firm* — Barnes & Thornburg LLP

(57) ABSTRACT

Various embodiments of unilateral implant holders and related methods are disclosed herein. An exemplary unilateral implant holder can include a surgical instrument that includes a unilateral locking mechanism arranged at a distal end of the instrument for rigidly holding onto a unilateral portion of the implant. The locking mechanism can be configured to lock onto a unilateral portion of the implant such that access to the implant is not blocked. By engaging the instrument's locking mechanism with a counterpart locking interface defined in an implant, sufficient clamping force can be applied by the locking mechanism to resist multi-directional forces exerted on the implant during a surgical procedure. The surgical instrument can be a stand-alone unilateral implant holder. The surgical instrument can be configured to perform a surgical task while concurrently holding the implant in place using the unilateral locking mechanism.

23 Claims, 27 Drawing Sheets

(52) U.S. Cl.
CPC ...... *A61B 17/7076* (2013.01); *A61B 17/7082* (2013.01); *A61B 17/7091* (2013.01); *A61B 2017/00477* (2013.01)

(58) Field of Classification Search
CPC ............ A61B 17/7074; A61B 17/7079; A61B 2017/681; A61B 17/7008
USPC ........................................ 606/250–279, 86 A
See application file for complete search history.

(56) References Cited

U.S. PATENT DOCUMENTS

| | | |
|---|---|---|
| 1,628,144 A | 5/1927 | Herrmann |
| 1,709,766 A | 4/1929 | Bolton |
| 1,889,330 A | 11/1932 | Humes et al. |
| 1,925,385 A | 9/1933 | Humes et al. |
| 2,113,246 A | 4/1938 | Frederick |
| 2,248,054 A | 7/1941 | Becker |
| 2,248,057 A | 7/1941 | Bond |
| 2,291,413 A | 7/1942 | Siebrandt |
| 2,370,407 A | 2/1945 | McCartney |
| 2,800,820 A | 7/1957 | Retterath |
| 3,960,147 A | 6/1976 | Murray |
| 4,237,875 A | 12/1980 | Termanini |
| 4,271,836 A | 6/1981 | Bacal et al. |
| 4,411,259 A | 10/1983 | Drummond |
| 4,445,513 A | 5/1984 | Ulrich et al. |
| 4,655,223 A | 4/1987 | Kim |
| 4,809,695 A | 3/1989 | Gwathmey et al. |
| 4,896,661 A | 1/1990 | Bogert et al. |
| 5,014,407 A | 5/1991 | Boughten et al. |
| 5,020,519 A | 6/1991 | Hayes et al. |
| D343,000 S | 1/1994 | Olson |
| D346,217 S | 4/1994 | Sparker et al. |
| 5,306,248 A | 4/1994 | Barrington |
| 5,364,397 A | 11/1994 | Hayes et al. |
| 5,391,170 A | 2/1995 | McGuire et al. |
| 5,429,641 A | 7/1995 | Gotfried et al. |
| 5,431,658 A | 7/1995 | Moskovich |
| 5,484,440 A | 1/1996 | Allard |
| 5,545,165 A | 8/1996 | Biedermann et al. |
| 5,551,320 A | 9/1996 | Horobec et al. |
| 5,616,143 A | 4/1997 | Schlapfer et al. |
| 5,649,931 A | 7/1997 | Bryant et al. |
| 5,672,175 A | 9/1997 | Martin |
| 5,683,399 A | 11/1997 | Jones |
| 5,697,933 A | 12/1997 | Gundlapalli et al. |
| 5,707,371 A | 1/1998 | Metz-Stavenhagen et al. |
| D390,954 S | 2/1998 | Kumar et al. |
| 5,720,751 A | 2/1998 | Jackson |
| 5,725,532 A | 3/1998 | Shoemaker |
| 5,746,757 A | 5/1998 | McGuire |
| 5,782,831 A | 7/1998 | Sherman et al. |
| 5,810,878 A | 9/1998 | Burel et al. |
| 5,910,141 A | 6/1999 | Morrison et al. |
| 5,941,885 A | 8/1999 | Jackson |
| 5,951,564 A | 9/1999 | Schroder et al. |
| 5,951,579 A | 9/1999 | Dykes |
| 6,010,509 A | 1/2000 | Delgado et al. |
| 6,036,692 A | 3/2000 | Burel et al. |
| 6,099,528 A | 8/2000 | Saurat et al. |
| 6,123,707 A | 9/2000 | Wagner |
| 6,139,549 A | 10/2000 | Keller |
| 6,183,472 B1 | 2/2001 | Lutz |
| 6,210,330 B1 | 4/2001 | Tepper et al. |
| 6,251,112 B1 | 6/2001 | Jackson |
| 6,258,090 B1 | 7/2001 | Jackson |
| 6,371,973 B1 | 4/2002 | Tepper et al. |
| 6,413,258 B1 | 7/2002 | Bernhardt, Jr. |
| 6,440,133 B1 | 8/2002 | Beale et al. |
| 6,440,142 B1 | 8/2002 | Ralph et al. |
| 6,440,144 B1 | 8/2002 | Bacher |
| 6,511,484 B2 | 1/2003 | Torode et al. |
| 6,530,929 B1 | 3/2003 | Justis et al. |
| 6,554,832 B2 | 4/2003 | Shluzas |
| 6,589,249 B2 | 7/2003 | Sater et al. |
| 6,648,888 B1 | 11/2003 | Shluzas |
| 6,660,006 B2 | 12/2003 | Markworth et al. |
| 6,676,661 B1 | 1/2004 | Martin Benlloch et al. |
| 6,726,692 B2 | 4/2004 | Bette et al. |
| 6,743,231 B1 | 6/2004 | Gray et al. |
| 6,746,449 B2 | 6/2004 | Jones et al. |
| 6,752,832 B2 | 6/2004 | Neumann |
| 6,755,829 B1 | 6/2004 | Bono et al. |
| 6,790,208 B2 | 9/2004 | Oribe et al. |
| 6,790,209 B2 | 9/2004 | Beale et al. |
| 6,827,722 B1 | 12/2004 | Schoenefeld |
| 7,081,117 B2 | 7/2006 | Bono et al. |
| 7,083,621 B2 | 8/2006 | Shaolian et al. |
| 7,090,677 B2 | 8/2006 | Fallin et al. |
| 7,156,849 B2 | 1/2007 | Dunbar et al. |
| 7,179,254 B2 | 2/2007 | Pendekanti et al. |
| 7,179,261 B2 | 2/2007 | Sicvol et al. |
| 7,189,234 B2 | 3/2007 | Zucherman et al. |
| 7,278,995 B2 | 10/2007 | Nichols et al. |
| 7,320,689 B2 | 1/2008 | Keller |
| 7,371,239 B2 | 5/2008 | Dec et al. |
| 7,462,182 B2 | 12/2008 | Lim |
| 7,481,813 B1 | 1/2009 | Purcell |
| 7,485,120 B2 | 2/2009 | Ray |
| 7,491,207 B2 | 2/2009 | Keyer et al. |
| 7,527,638 B2 | 5/2009 | Anderson et al. |
| 7,572,281 B2 | 8/2009 | Runco et al. |
| 7,621,918 B2 | 11/2009 | Jackson |
| 7,651,502 B2 | 1/2010 | Jackson |
| 7,666,188 B2 | 2/2010 | Anderson et al. |
| 7,708,763 B2 | 5/2010 | Selover et al. |
| 7,776,040 B2 | 8/2010 | Markworth et al. |
| 7,806,912 B2 | 10/2010 | Lawton et al. |
| 7,824,411 B2 | 11/2010 | Varieur et al. |
| 7,824,413 B2 | 11/2010 | Varieur et al. |
| 7,842,044 B2 | 11/2010 | Runco et al. |
| 7,867,237 B2 | 1/2011 | Stad et al. |
| 7,887,539 B2 | 2/2011 | Dunbar, Jr. et al. |
| 7,887,541 B2 | 2/2011 | Runco et al. |
| 7,901,434 B2 | 3/2011 | Drewry et al. |
| 7,922,724 B2 | 4/2011 | Lim |
| 7,931,677 B2 | 4/2011 | Abdelgany |
| 7,988,698 B2 | 8/2011 | Rosenberg et al. |
| 8,109,974 B2 | 2/2012 | Boomer et al. |
| 8,172,847 B2 | 5/2012 | Dziedzic et al. |
| 8,192,438 B2 | 6/2012 | Garamszegi |
| 8,216,241 B2 | 7/2012 | Runco et al. |
| 8,235,997 B2 | 8/2012 | Hoffman et al. |
| 8,246,657 B1 | 8/2012 | Samuel |
| 8,298,269 B2 | 10/2012 | Null et al. |
| 8,303,595 B2 | 11/2012 | Jones |
| 8,308,774 B2 | 11/2012 | Hoffman et al. |
| 8,317,837 B2 | 11/2012 | Rezach et al. |
| 8,337,527 B2 | 12/2012 | Hawkins et al. |
| 8,343,165 B2 | 1/2013 | Berrevoets |
| 8,377,104 B2 | 2/2013 | Jones et al. |
| 8,394,109 B2 | 3/2013 | Hutton et al. |
| 8,430,916 B1 | 4/2013 | Winslow et al. |
| 8,439,922 B1 | 5/2013 | Arnold et al. |
| 8,460,308 B2 | 6/2013 | Marino et al. |
| 8,540,718 B2 | 9/2013 | Dauster et al. |
| 8,556,904 B2 | 10/2013 | Rezach et al. |
| 8,603,145 B2 | 12/2013 | Forton et al. |
| 8,617,165 B2 | 12/2013 | Harper |
| 8,636,742 B2 | 1/2014 | Runco et al. |
| 8,636,776 B2 | 1/2014 | Rosenberg et al. |
| 8,647,347 B2 | 2/2014 | Runco et al. |
| 8,657,857 B2 | 2/2014 | Dall et al. |
| 8,685,029 B2 | 4/2014 | Dziedzic et al. |
| 8,715,323 B2 | 5/2014 | Ballard et al. |
| 8,728,124 B2 | 5/2014 | Miller |
| 8,747,409 B2 | 6/2014 | Ichelmann et al. |
| 8,764,756 B2 | 7/2014 | Jones |
| 8,790,348 B2 | 7/2014 | Stad et al. |
| 8,795,283 B2 | 8/2014 | Petit |
| 8,828,056 B2 | 9/2014 | Buss et al. |
| 8,845,640 B2 | 9/2014 | McLean et al. |
| 8,845,649 B2 | 9/2014 | Jackson |

(56) References Cited

U.S. PATENT DOCUMENTS

| | | |
|---|---|---|
| 8,870,881 B2 | 10/2014 | Rezach et al. |
| 8,876,869 B1 | 11/2014 | Schafer et al. |
| 8,900,240 B2 | 12/2014 | White et al. |
| 8,906,062 B2 | 12/2014 | Nichols et al. |
| 8,932,296 B2 | 1/2015 | Neary et al. |
| 8,951,289 B2 | 2/2015 | Matityahu |
| 8,956,362 B2 | 2/2015 | Landry et al. |
| 8,979,848 B2 | 3/2015 | Butters et al. |
| 8,986,349 B1 | 3/2015 | German et al. |
| 9,044,272 B2 | 6/2015 | Shaffrey et al. |
| 9,044,274 B2 | 6/2015 | Gunn et al. |
| 9,078,705 B2 | 7/2015 | Matthis et al. |
| 9,078,709 B2 | 7/2015 | McBride |
| 9,084,634 B1 | 7/2015 | Lab et al. |
| 9,119,674 B2 | 9/2015 | Matthis et al. |
| 9,125,694 B2 | 9/2015 | Butler et al. |
| 9,149,307 B2 | 10/2015 | Sandstrom et al. |
| 9,155,567 B2 | 10/2015 | Auerbach et al. |
| 9,186,188 B2 | 11/2015 | Gleason et al. |
| 9,204,901 B2 | 12/2015 | Black et al. |
| 9,204,909 B2 | 12/2015 | Rezach et al. |
| 9,220,543 B2 | 12/2015 | Walker et al. |
| 9,247,969 B2 | 2/2016 | Nunley et al. |
| 9,254,150 B2 | 2/2016 | Biedermann et al. |
| 9,265,533 B2 | 2/2016 | Nelson et al. |
| 9,265,538 B2 | 2/2016 | Stad et al. |
| 9,271,768 B2 | 3/2016 | Artaki et al. |
| 9,283,002 B2 | 3/2016 | Larroque-Lahitette et al. |
| 9,308,030 B2 | 4/2016 | Manninen |
| 9,451,994 B1 | 9/2016 | Whipple et al. |
| 9,486,256 B1 | 11/2016 | Lish et al. |
| 9,492,205 B2 | 11/2016 | Alsup et al. |
| 9,498,261 B2 | 11/2016 | McClintock |
| 9,795,417 B2 | 10/2017 | Beger et al. |
| 10,238,432 B2 | 3/2019 | Carruth et al. |
| 10,299,839 B2 | 5/2019 | Sicvol et al. |
| 10,398,476 B2 | 9/2019 | Lee et al. |
| D914,210 S | 3/2021 | Koros |
| 10,966,762 B2 * | 4/2021 | Lee .................. A61B 17/7074 |
| 11,291,481 B2 | 4/2022 | Schmura et al. |
| 11,291,482 B2 | 4/2022 | Schmura et al. |
| 2001/0029376 A1 | 10/2001 | Sater et al. |
| 2002/0072752 A1 | 6/2002 | Zucherman et al. |
| 2002/0095153 A1 | 7/2002 | Jones et al. |
| 2003/0009168 A1 | 1/2003 | Beale et al. |
| 2003/0028195 A1 | 2/2003 | Bette |
| 2003/0083747 A1 | 5/2003 | Winterbottom et al. |
| 2003/0125750 A1 | 7/2003 | Zwirnmann et al. |
| 2003/0149438 A1 | 8/2003 | Nichols et al. |
| 2003/0171756 A1 | 9/2003 | Fallin et al. |
| 2003/0191370 A1 | 10/2003 | Phillips |
| 2003/0199872 A1 | 10/2003 | Markworth et al. |
| 2003/0208203 A1 | 11/2003 | Lim et al. |
| 2003/0225408 A1 | 12/2003 | Nichols et al. |
| 2004/0049191 A1 | 3/2004 | Markworth et al. |
| 2004/0147936 A1 | 7/2004 | Rosenberg et al. |
| 2004/0147937 A1 | 7/2004 | Dunbar et al. |
| 2004/0172057 A1 | 9/2004 | Guillebon et al. |
| 2004/0176779 A1 | 9/2004 | Casutt et al. |
| 2004/0220567 A1 | 11/2004 | Eisermann et al. |
| 2004/0254576 A1 | 12/2004 | Dunbar et al. |
| 2004/0267275 A1 | 12/2004 | Cournoyer et al. |
| 2005/0015094 A1 | 1/2005 | Keller |
| 2005/0015095 A1 | 1/2005 | Keller |
| 2005/0033299 A1 | 2/2005 | Shluzas |
| 2005/0051648 A1 | 3/2005 | Mercier |
| 2005/0055031 A1 | 3/2005 | Lim |
| 2005/0059969 A1 | 3/2005 | McKinley |
| 2005/0079909 A1 | 4/2005 | Singhaseni |
| 2005/0090824 A1 | 4/2005 | Shluzas et al. |
| 2005/0131408 A1 | 6/2005 | Sicvol et al. |
| 2005/0131420 A1 | 6/2005 | Techiera et al. |
| 2005/0131421 A1 | 6/2005 | Anderson et al. |
| 2005/0131422 A1 | 6/2005 | Anderson et al. |
| 2005/0143749 A1 | 6/2005 | Zalenski et al. |
| 2005/0149036 A1 | 7/2005 | Varieur et al. |
| 2005/0149048 A1 | 7/2005 | Leport et al. |
| 2005/0149053 A1 | 7/2005 | Varieur et al. |
| 2005/0192570 A1 | 9/2005 | Jackson |
| 2005/0192579 A1 | 9/2005 | Jackson |
| 2005/0228392 A1 | 10/2005 | Keyer et al. |
| 2005/0261702 A1 | 11/2005 | Oribe et al. |
| 2006/0009775 A1 | 1/2006 | Dec et al. |
| 2006/0025768 A1 | 2/2006 | Iott et al. |
| 2006/0036254 A1 | 2/2006 | Lim |
| 2006/0036260 A1 | 2/2006 | Runco et al. |
| 2006/0069391 A1 | 3/2006 | Jackson |
| 2006/0074418 A1 | 4/2006 | Jackson |
| 2006/0079892 A1 | 4/2006 | Roychowdhury et al. |
| 2006/0079909 A1 | 4/2006 | Runco et al. |
| 2006/0089651 A1 | 4/2006 | Trudeau et al. |
| 2006/0095035 A1 | 5/2006 | Jones et al. |
| 2006/0111712 A1 | 5/2006 | Jackson |
| 2006/0111713 A1 | 5/2006 | Jackson |
| 2006/0111730 A1 | 5/2006 | Hay |
| 2006/0166534 A1 | 7/2006 | Brumfield et al. |
| 2006/0166535 A1 | 7/2006 | Brumfield et al. |
| 2006/0229611 A1 | 10/2006 | Avery et al. |
| 2006/0233597 A1 | 10/2006 | Ensign et al. |
| 2006/0293692 A1 | 12/2006 | Whipple et al. |
| 2007/0093849 A1 | 4/2007 | Jones et al. |
| 2007/0100347 A1 | 5/2007 | Stad et al. |
| 2007/0129731 A1 | 6/2007 | Sicvol et al. |
| 2007/0161998 A1 | 7/2007 | Whipple |
| 2007/0167954 A1 | 7/2007 | Sicvol et al. |
| 2007/0173831 A1 | 7/2007 | Abdou |
| 2007/0185375 A1 | 8/2007 | Stad et al. |
| 2007/0213722 A1 | 9/2007 | Jones et al. |
| 2007/0233097 A1 | 10/2007 | Anderson et al. |
| 2007/0260261 A1 | 11/2007 | Runco et al. |
| 2007/0270817 A1 | 11/2007 | Rezach |
| 2007/0270880 A1 | 11/2007 | Lindemann et al. |
| 2007/0282337 A1 | 12/2007 | Garamszegi |
| 2008/0015601 A1 | 1/2008 | Castro et al. |
| 2008/0058805 A1 | 3/2008 | Stuart |
| 2008/0077134 A1 | 3/2008 | Dziedzic et al. |
| 2008/0077135 A1 | 3/2008 | Stad et al. |
| 2008/0154277 A1 | 6/2008 | Machalk et al. |
| 2008/0195155 A1 | 8/2008 | Hoffman et al. |
| 2008/0228233 A1 * | 9/2008 | Hoffman ............ A61B 17/7088 606/86 A |
| 2008/0243190 A1 | 10/2008 | Dziedzic et al. |
| 2008/0255574 A1 | 10/2008 | Dye |
| 2009/0030419 A1 | 1/2009 | Runco et al. |
| 2009/0030420 A1 | 1/2009 | Runco et al. |
| 2009/0054902 A1 | 2/2009 | Mickiewicz et al. |
| 2009/0082811 A1 | 3/2009 | Stad et al. |
| 2009/0088764 A1 | 4/2009 | Stad et al. |
| 2009/0105712 A1 | 4/2009 | Dauster et al. |
| 2009/0138056 A1 | 5/2009 | Anderson et al. |
| 2009/0143828 A1 | 6/2009 | Stad et al. |
| 2009/0312804 A1 | 12/2009 | Gamache et al. |
| 2010/0137915 A1 | 6/2010 | Anderson et al. |
| 2011/0034961 A1 | 2/2011 | Runco et al. |
| 2011/0034962 A1 | 2/2011 | Dunbar, Jr. et al. |
| 2011/0093022 A1 | 4/2011 | Runco et al. |
| 2011/0144695 A1 | 6/2011 | Rosenberg et al. |
| 2011/0208254 A1 | 8/2011 | Villa et al. |
| 2012/0029571 A1 | 2/2012 | Schwab et al. |
| 2012/0053643 A1 | 3/2012 | Harper |
| 2012/0143265 A1 | 6/2012 | Biedermann et al. |
| 2012/0179214 A1 | 7/2012 | Geist et al. |
| 2012/0191144 A1 | 7/2012 | Peultier et al. |
| 2012/0203291 A1 | 8/2012 | Boulaine |
| 2012/0253413 A1 | 10/2012 | Runco et al. |
| 2013/0018419 A1 | 1/2013 | Rezach et al. |
| 2013/0066385 A1 | 3/2013 | Benoist |
| 2013/0079826 A1 | 3/2013 | Simonson |
| 2013/0085534 A1 | 4/2013 | Hainard et al. |
| 2013/0123854 A1 | 5/2013 | Kondrashov et al. |
| 2013/0245702 A1 | 9/2013 | McBride |
| 2014/0012337 A1 | 1/2014 | Biedermann et al. |
| 2014/0018858 A1 | 1/2014 | Laeng et al. |
| 2014/0074106 A1 | 3/2014 | Shin |

(56) References Cited

U.S. PATENT DOCUMENTS

| | | |
|---|---|---|
| 2014/0094858 A1 | 4/2014 | Picetti et al. |
| 2014/0114363 A1 | 4/2014 | Stevenson et al. |
| 2014/0148865 A1 | 5/2014 | Hennard et al. |
| 2014/0163625 A1 | 6/2014 | Meyer et al. |
| 2014/0180298 A1 | 6/2014 | Stevenson et al. |
| 2014/0276896 A1 | 9/2014 | Harper |
| 2014/0277160 A1 | 9/2014 | Ziolo |
| 2014/0277170 A1 | 9/2014 | Barett et al. |
| 2014/0277206 A1 | 9/2014 | Reitblat et al. |
| 2014/0296862 A1 | 10/2014 | Stad et al. |
| 2014/0311264 A1 | 10/2014 | Black et al. |
| 2014/0316475 A1 | 10/2014 | Parikh et al. |
| 2015/0057707 A1 | 2/2015 | Barrus et al. |
| 2015/0066042 A1 | 3/2015 | Cummins et al. |
| 2015/0100097 A1 | 4/2015 | Barrus |
| 2015/0100098 A1 | 4/2015 | Moore |
| 2015/0105832 A1 | 4/2015 | Gleason et al. |
| 2015/0112397 A1 | 4/2015 | Petit |
| 2015/0173803 A1 | 6/2015 | Droulout |
| 2015/0182265 A1 | 7/2015 | Biedermann et al. |
| 2015/0196328 A1 | 7/2015 | Hirschl et al. |
| 2015/0201971 A1 | 7/2015 | Gaines et al. |
| 2015/0257798 A1 | 9/2015 | Biedermann et al. |
| 2015/0359568 A1 | 12/2015 | Rezach |
| 2016/0022317 A1 | 1/2016 | Kraus |
| 2016/0066967 A1 | 3/2016 | Jackson et al. |
| 2016/0151093 A1 | 6/2016 | Barry et al. |
| 2016/0242825 A1 | 8/2016 | Simpson et al. |
| 2017/0265901 A1 | 9/2017 | Hawkins et al. |
| 2017/0333087 A1 | 11/2017 | Lee et al. |
| 2017/0333088 A1 | 11/2017 | Lee et al. |
| 2018/0014858 A1 | 1/2018 | Biester et al. |
| 2018/0161073 A1 | 6/2018 | Lee et al. |
| 2018/0185072 A1 | 7/2018 | Rubin et al. |
| 2018/0228518 A1 | 8/2018 | Carruth et al. |
| 2018/0280062 A1 | 10/2018 | Lee et al. |
| 2019/0117280 A1 | 4/2019 | Avidano et al. |
| 2019/0193541 A1 | 6/2019 | Takeda |
| 2020/0297395 A1 | 9/2020 | Schmura et al. |
| 2020/0297396 A1 | 9/2020 | Schmura et al. |
| 2021/0059725 A1 | 3/2021 | Avidano et al. |
| 2023/0157736 A1 | 5/2023 | Cromer et al. |

FOREIGN PATENT DOCUMENTS

| | | |
|---|---|---|
| DE | 29806563 U1 | 6/1998 |
| EP | 0 948 939 A2 | 10/1999 |
| EP | 1 574 175 A1 | 9/2005 |
| EP | 1 648 320 A2 | 4/2006 |
| EP | 1 796 564 A1 | 6/2007 |
| EP | 2 004 079 A2 | 12/2008 |
| FR | 2677242 A1 | 12/1992 |
| FR | 2680314 A1 | 2/1993 |
| FR | 2729291 A1 | 7/1996 |
| WO | 96/021396 A1 | 7/1996 |
| WO | 02/080787 A3 | 4/2003 |
| WO | 03/028566 A1 | 4/2003 |
| WO | 2005/006948 A2 | 1/2005 |
| WO | 2005/058173 A1 | 6/2005 |
| WO | 2006/020443 A1 | 2/2006 |
| WO | 2010/045301 A1 | 4/2010 |

OTHER PUBLICATIONS

U.S. Appl. No. 16/360,193, filed Mar. 21, 2019, Rod Reducers and Related Methods.

U.S. Appl. No. 16/360,199, filed Mar. 21, 2019, Rod Reducers and Related Methods.

U.S. Appl. No. 29/684,449, filed Mar. 21, 2019, Kerrison Rod Reducer.

International Search Report and Written Opinion for PCT/US2018/065497, dated Jul. 8, 2019 (22 pages).

U.S. Appl. No. 17/989,797, filed Nov. 18, 2022, Reducer Locking Mechanisms and Methods of Use.

International Search Report and Written Opinion for PCT/EP2022/084215, dated Mar. 15, 2023(12 pages).

* cited by examiner

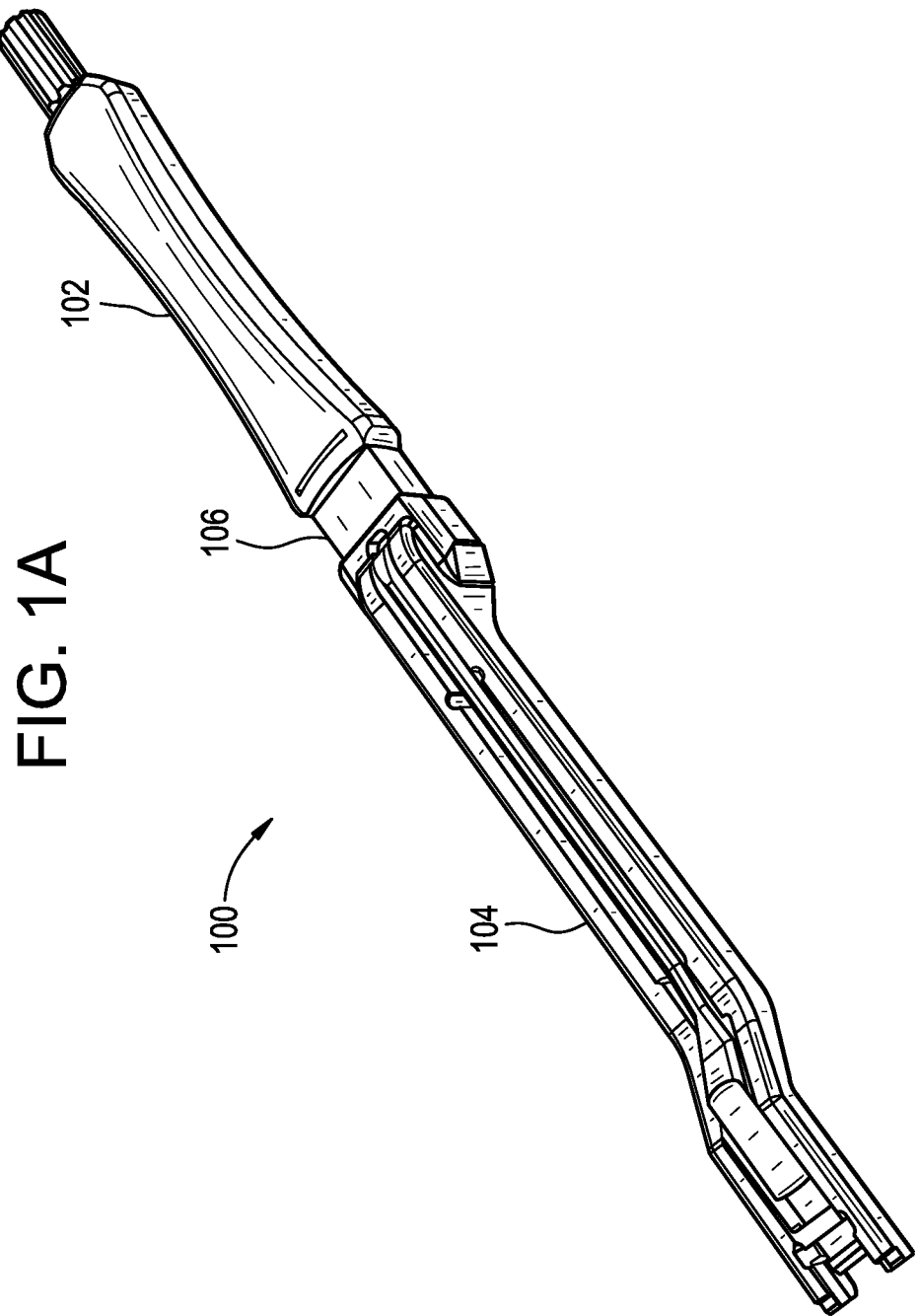

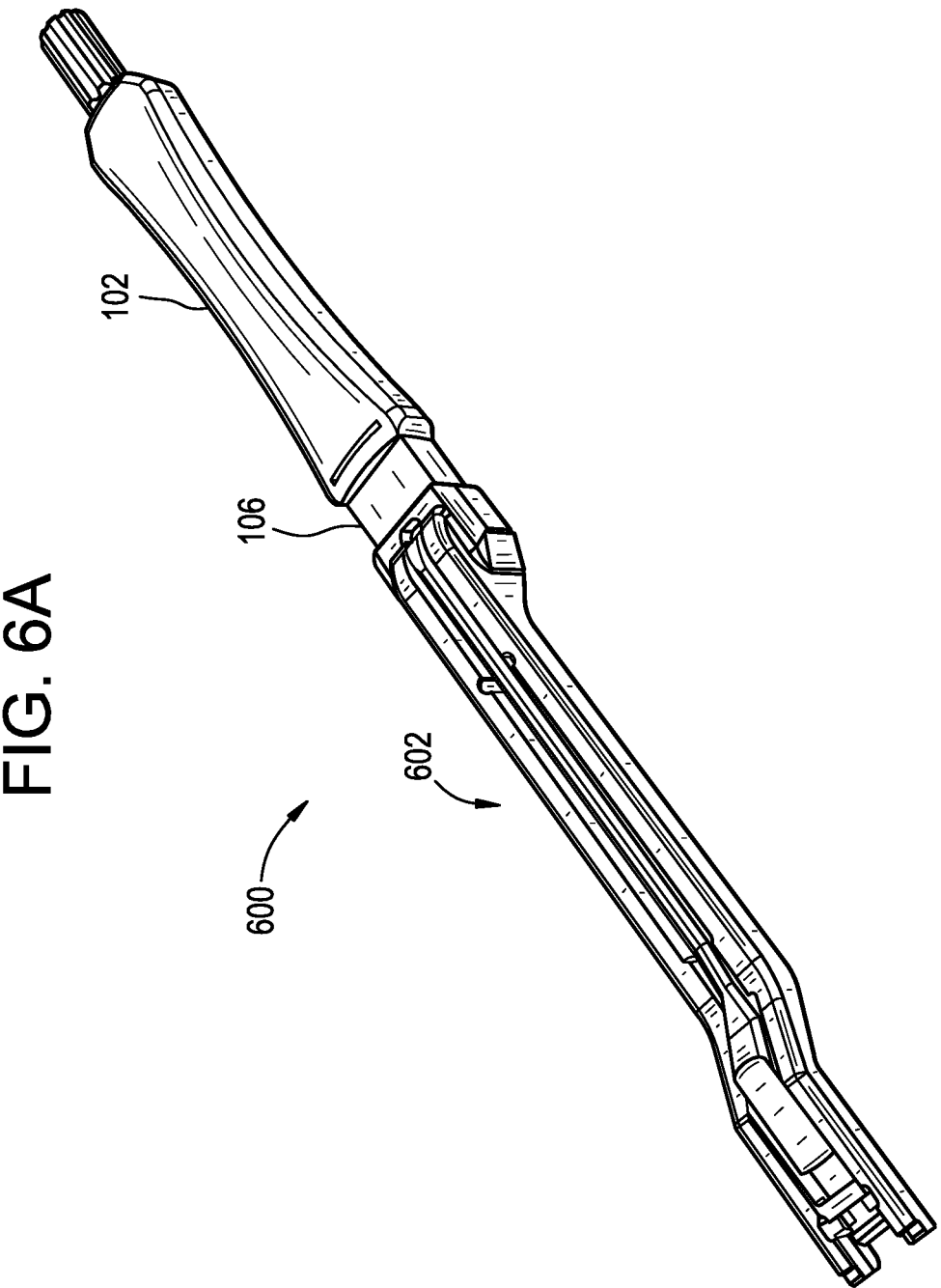

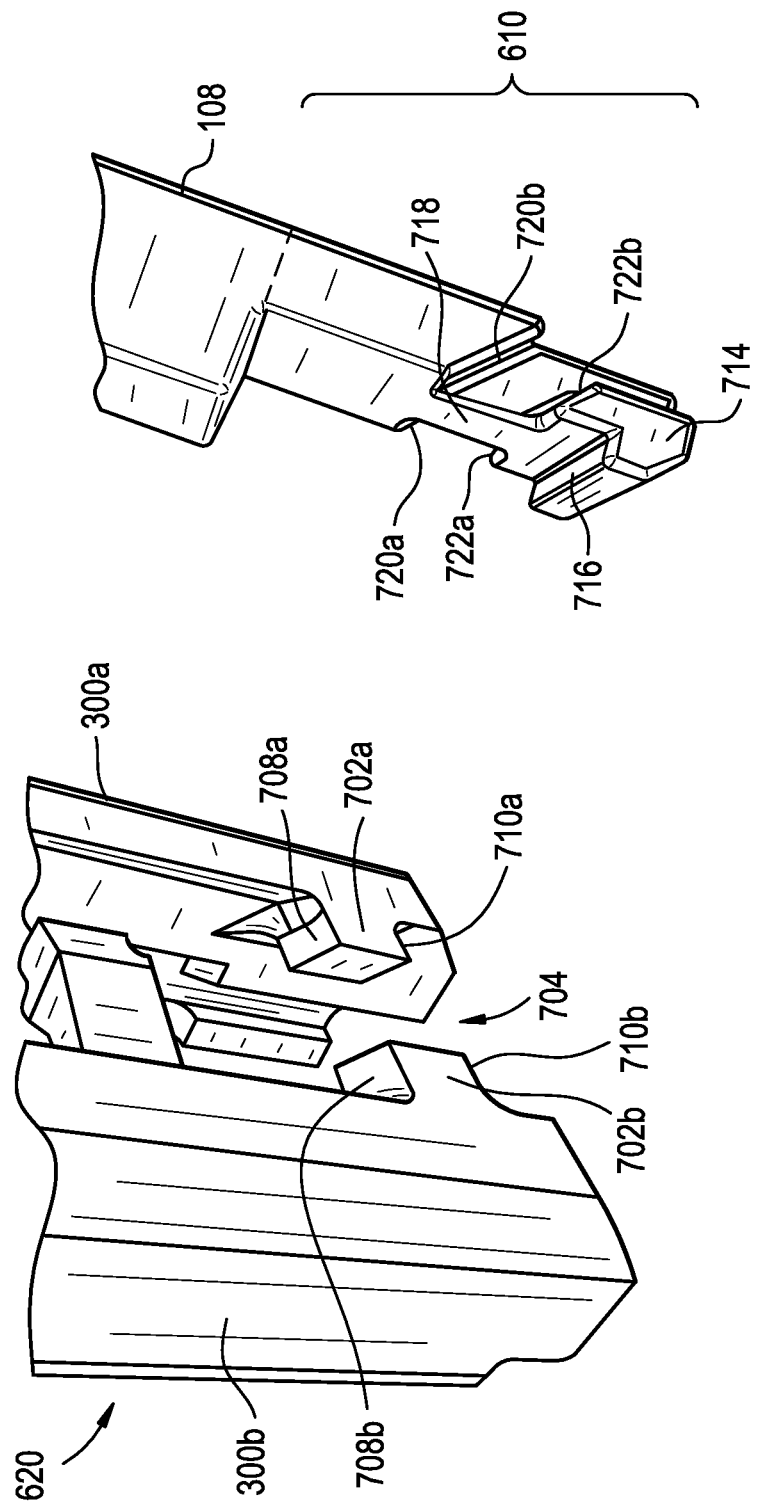

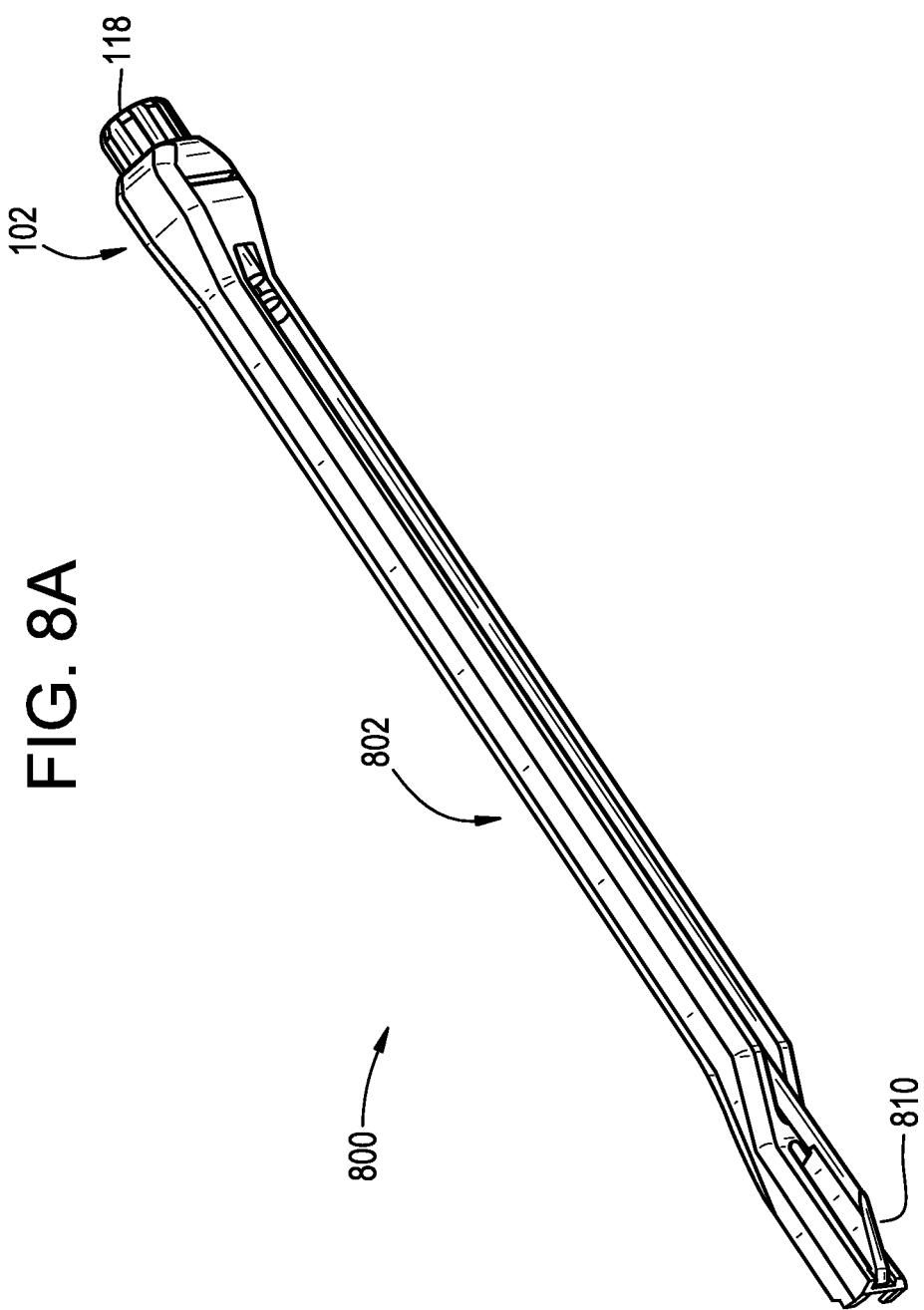

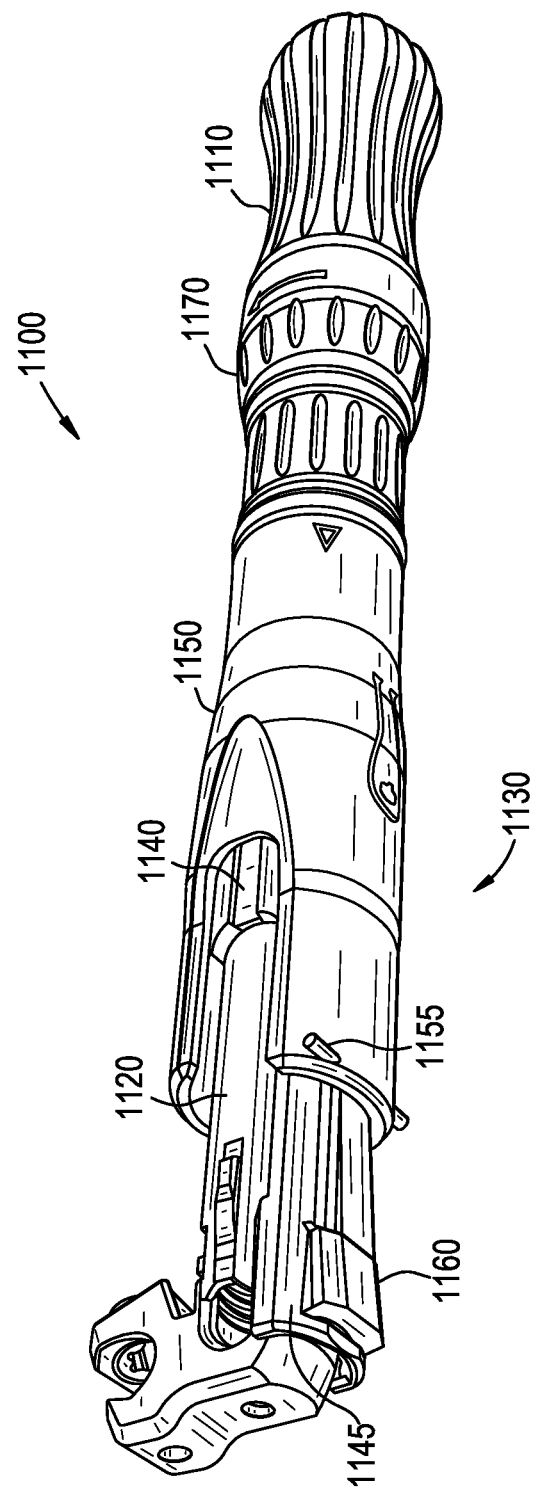

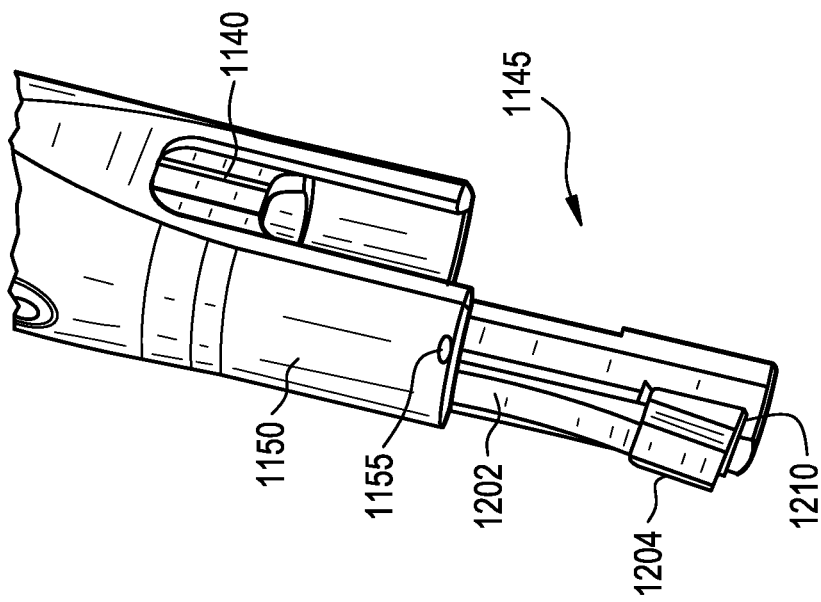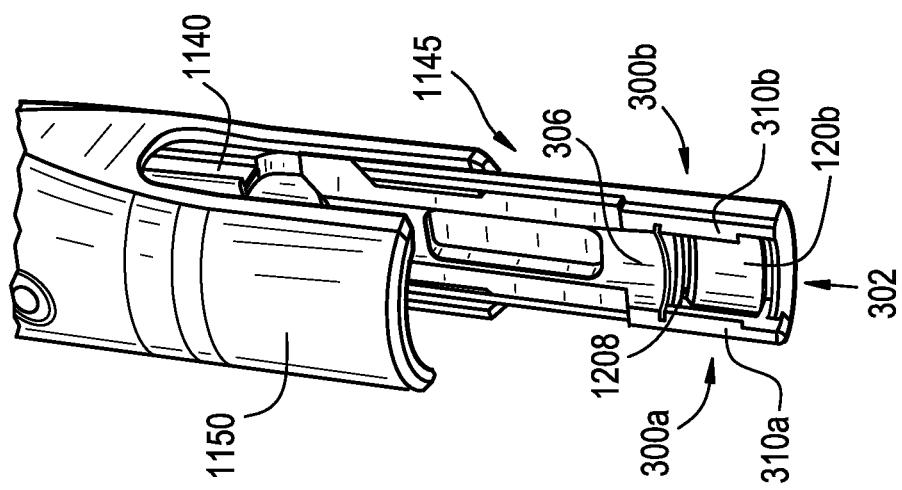

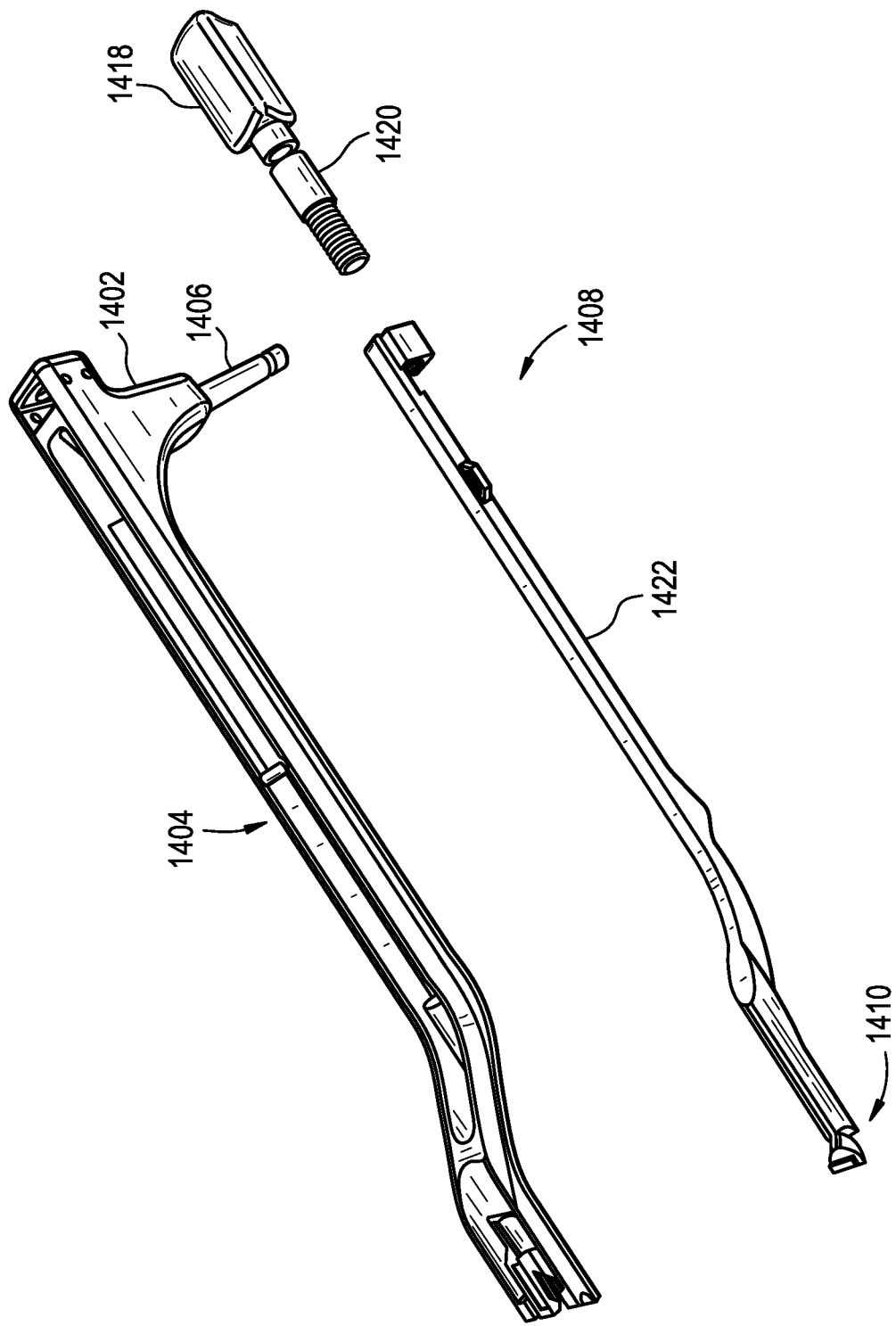

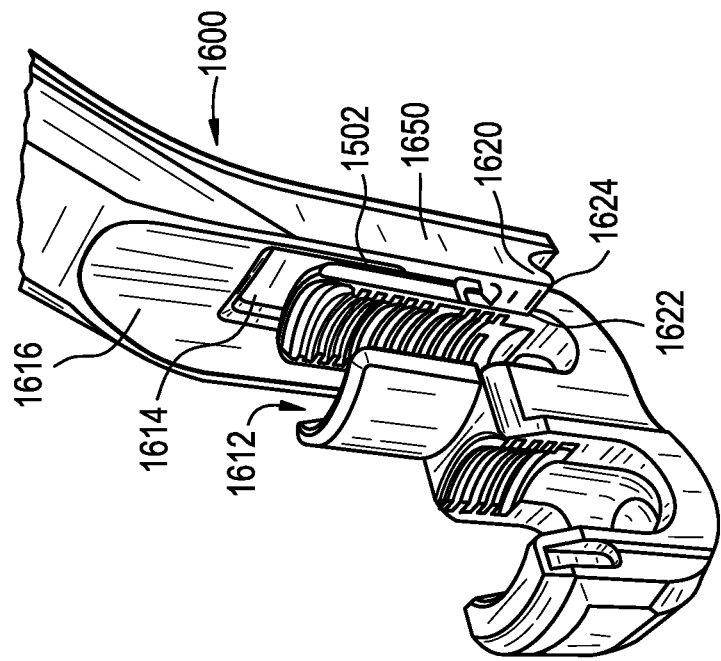
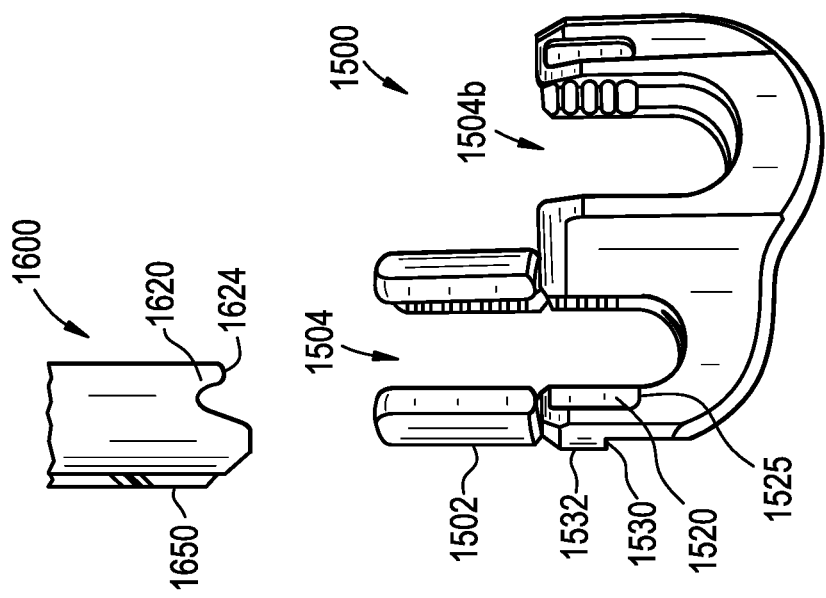

UNILATERAL IMPLANT HOLDERS AND RELATED METHODS

CROSS-REFERENCE TO RELATED APPLICATIONS

This application is a continuation of U.S. patent application Ser. No. 15/843,618, filed on Dec. 15, 2017, which is incorporated herein by reference in its entirety.

FIELD

Unilateral implant holders and related methods are disclosed herein.

BACKGROUND

Fixation systems can be used in orthopedic surgery or neurosurgery to maintain a desired spatial relationship between multiple bones or bone fragments. For example, various conditions of the spine, such as fractures, deformities, and degenerative disorders, can be treated by attaching a spinal fixation system to one or more vertebrae. Such systems may include a spinal fixation element, such as a rod, that is coupled to the vertebrae by one or more bone anchors, such as screws or hooks. The fixation system can also include various other implants, such as connectors for attaching multiple rods to one another. Once installed, the fixation system holds the vertebrae in a desired position until healing or spinal fusion can occur, or for some other period of time.

There may be various difficulties in manipulating and handling implants at a surgical site, particularly in the case of minimally-invasive procedures or procedures that involve areas with narrow anatomical constraints, such as the cervical spine. Existing surgical pick-up tools, such as forceps and tweezers, may fail to provide sufficient clamping force to resist the multi-directional forces exerted on the implant as it is manipulated within the surgical site, making it difficult to position the implant and increasing the risk of dropping the implant. Insertion instruments that rigidly attach to the implant may have considerable bulk and can limit the degree or manner in which the implant can be manipulated, impede insertion of a rod or other component into the implant, or cause other challenges.

SUMMARY

Various embodiments of unilateral implant holders and related methods are disclosed herein. An exemplary unilateral implant holder can include a surgical instrument that includes a unilateral locking mechanism arranged at a distal end of the instrument for rigidly holding an implant, such as a rod-to-rod connector or bone anchor. The locking mechanism can be configured to lock onto one end of an implant (i.e., a unilateral portion). For example, the locking mechanism can be configured to lock onto a unilateral portion of the implant such that access to an open recess or slot (e.g., for receiving a rod or a set screw) is not blocked. The locking mechanism can be configured to lock onto the unilateral portion of the implant by engaging a counterpart locking interface defined therein. By engaging the instrument's locking mechanism with the implant's counterpart locking interface, sufficient clamping force can be applied by the locking mechanism to resist multi-directional forces exerted on the implant during a surgical procedure. In some embodiments, the surgical instrument can be a stand-alone unilateral implant holder. In some embodiments, the surgical instrument can be configured to perform a surgical task while concurrently holding the implant in place using a unilateral locking mechanism. For example, the surgical instrument can include or be used with a rod reducer, a set screw inserter, or the like.

In some embodiments, a surgical instrument configured to unilaterally hold an implant can include a handle and a unilateral locking mechanism. The unilateral locking mechanism can include an elongated body having a proximal end coupled to the handle and a distal end defining multiple locking elements configured to engage a unilateral portion of the implant. The locking elements can include a proximal facing bearing surface, a distal-facing bearing surface, and a lateral-facing bearing surface configured to engage counterpart surfaces of the unilateral portion of the implant. The proximal-facing bearing surface can be formed on a clasp movable upwards to engage the implant. The locking elements of the unilateral locking mechanism can be configured to engage the unilateral portion of the implant such that the locking elements are laterally offset from a proximal-distal axis of an open recess of the implant. The body of the unilateral locking mechanism can define a pair of spaced apart arms forming an implant-receiving pocket therebetween.

The distal-facing bearing surface of the unilateral locking mechanism can extend transversely between the pair of spaced apart arms. The distal-facing bearing surface can be configured to contact a counterpart proximal-facing bearing surface of the unilateral portion of the implant and to thereby constrain longitudinal movement of the implant in a proximal direction. The distal-facing bearing surface can be formed on a stop beam.

The lateral-facing bearing surface of the unilateral locking mechanism can protrude longitudinally along at least one of opposing faces of the pair of spaced apart arms at or adjacent to a front of the pocket. The lateral-facing bearing surface can be configured to mate and slide along a lateral-facing counterpart groove formed in the unilateral portion of the implant and to thereby constrain lateral movements of the implant. The lateral-facing bearing surface can be formed on an insertion tab.

The proximal-facing bearing surface of the clasp can be disposed between opposing faces of the pair of spaced apart arms at or adjacent to a back of the pocket. The proximal-facing bearing surface can be configured to interlock with a counterpart distal-facing bearing surface of the unilateral portion of the implant and to thereby constrain longitudinal movement of the implant in a distal direction. The proximal-facing bearing surface can be formed on a lateral protrusion of the clasp.

The surgical instrument can include a control shaft having a proximal end moveably coupled to the handle and a distal end coupled to the clasp. The control shaft can be configured to move longitudinally in a proximal direction and to thereby move the clasp into a locked configuration in which the proximal-facing bearing surface of the lateral protrusion engages the counterpart distal-facing bearing surface of the unilateral portion of the implant. The control shaft can be configured to move longitudinally in a distal direction and to thereby move the clasp into an unlocked configuration in which the proximal-facing bearing surface of the lateral protrusion releases the counterpart distal-facing bearing surface of the unilateral portion of the implant. The clasp can be movable upward and inward to lock the surgical instrument onto the unilateral portion of the implant and can be movable downward and outward to unlock the surgical instrument from the unilateral portion of the implant. The control shaft can be configured to move longitudinally in a proximal direction and thereby move the clasp upward to engage the unilateral portion of the implant and lock the surgical instrument onto the implant.

The surgical instrument can include a pin and slot interface defined between the control shaft and the body of the unilateral locking mechanism to guide movements of the clasp between the locked configuration and unlocked configuration. A spring element can be defined in a surface of the handle portion and configured to exert a force against the second control shaft so that the pin slides along an edge of the slot interface. The elongated body of the unilateral locking mechanism can include one or more body segments angled to offset a longitudinal axis of the handle from a proximal-distal axis of an open recess defined in a body of the implant.

In some embodiments, the surgical instrument can include a clasp guide. The clasp guide can include at least a pair of clasp guide structures protruding between opposing faces of the pair of spaced apart arms at or adjacent to a back of the pocket. The pair of clasp guide structures can have proximal-facing ramped bearing surfaces configured to urge the clasp upward and inward towards the locked configuration in response to proximal movements of the control shaft. The pair of clasp guide structures can have distal-facing ramped bearing surfaces configured to guide the clasp downward and outward away from the locked configuration in response to distal movements of the control shaft.

The clasp can have a narrow body region formed between a proximal portion and a distal portion of the clasp and configured to pass through a spatial region formed between opposing faces of the pair of clasp guide structures. The clasp can include at least a pair of counterpart distal-facing ramped bearing surfaces extending laterally at a proximal end of the narrow body region. The counterpart distal-facing ramped bearing surfaces of the clasp can be configured to slide against the proximal-facing ramped bearing surfaces of the clasp guide structures. The clasp can include at least a pair of counterpart proximal-facing ramped bearing surfaces extending laterally at a distal end of the narrow body region. The counterpart proximal-facing ramped bearing surfaces of the clasp can be configured to slide against the distal-facing ramped bearing surfaces of the clasp guide structures.

In some embodiments, the surgical instrument can include a clasp guide. The clasp guide can include a proximal-facing ramped bearing surface, at least a pair of distal-facing ramped bearing surfaces, and a lateral-facing vertical bearing surface for guiding lateral movements and longitudinal movements of the clasp between the locked configuration and the unlocked configuration.

The proximal-facing ramped bearing surface can be formed on a lateral beam that extends transversely between the distal ends of the pair of spaced apart arms. The proximal-facing ramped bearing surface can be obliquely angled to engage a counterpart distal-facing ramped bearing surface of the clasp in response to distal movements of the control shaft and thereby guide lateral movements of the clasp outward away from the locked configuration.

The pair of distal-facing ramped bearing surfaces can be formed on distal ends of laterally opposing guide rails that extend longitudinally along the pair of spaced apart arms. The pair of distal-facing ramped bearing surfaces can be obliquely angled to engage a pair of counterpart proximal-facing ramped bearing surfaces of the clasp in response to proximal movements of the control shaft and thereby guide lateral movements of the clasp inward towards the locked configuration.

The lateral-facing vertical bearing surface can extend transversely between laterally opposing guide rails that extend longitudinally along the pair of spaced apart arms. The vertical bearing surface can be configured to engage a counterpart vertical bearing surface of the clasp and thereby guide longitudinal movements of the clasp between the locked and unlocked configurations in response to corresponding movements of the control shaft.

In some embodiments, the distal-facing bearing surface and the lateral-facing bearing surface can be formed on one or more prongs extending from the distal end of the elongated body of the unilateral locking mechanism. The lateral-facing bearing surface of each prong can slide along a lateral-facing counterpart groove formed in the unilateral portion of the implant to constrain lateral movements of the implant. The distal-facing bearing surface of each prong can contact a distal edge of the lateral-facing counterpart groove of the implant to constrain longitudinal movements of the implant in a proximal direction.

The surgical instrument can include a pocket formed in the distal end of the elongated body of the unilateral locking mechanism. The pocket can have a size and shape that accommodates the unilateral portion of the implant. The proximal-facing bearing surface of the clasp can be disposed through an opening at the back of the pocket. The proximal-facing bearing surface of the clasp can move upwards to interlock with a counterpart distal-facing bearing surface of the unilateral portion of the implant to constrain longitudinal movement of the implant in a distal direction. The size and the shape of the pocket can be configured to further accommodate a reduction tab proximally extending from the unilateral portion of the implant. The size and the shape of the pocket can be configured to further accommodate a distal head of an auxiliary instrument. The distal head of the auxiliary instrument can be a bell-shaped head of a nut driver. The surgical instrument can include a counter-torque lever extending substantially perpendicular to the handle.

In some embodiments, a surgical instrument configured to unilaterally hold an implant can include a handle and a unilateral locking mechanism. The unilateral locking mechanism can include an elongated body having a proximal end coupled to the handle and a distal end defining multiple locking elements configured to engage a unilateral portion of the implant. The unilateral locking mechanism can include a tubular locking shaft, a partial tubular locking shaft segment, a clasp, and a locking sleeve. The partial tubular locking shaft segment can be formed at a distal end of the tubular locking shaft. A window can be formed in the partial tubular locking shaft segment exposing an implant-receiving pocket. The clasp can have a proximal clasp portion fixedly attached to an outer surface of the partial tubular shaft segment and a free distal clasp portion aligned with the window. The locking sleeve can be configured to slide longitudinally over the tubular locking shaft and the partial tubular shaft segment.

The free distal clasp portion can enter the window towards the implant-receiving pocket in response to the locking sleeve sliding distally over the free distal clasp portion. The free distal clasp portion can exit the window away from the implant-receiving pocket in response to the locking sleeve sliding proximally away from the free distal clasp portion. The free distal clasp portion can define a surface protrusion configured to engage a counterpart groove formed in the unilateral portion of the implant. The surface protrusion of the free distal clasp portion can be configured to engage the counterpart groove of the implant in response to entering the window towards the implant-receiving pocket. The surface protrusion can be configured to disengage the counterpart groove of the implant in response to the free distal clasp portion exiting the window away from the implant-receiving pocket.

The surgical instrument can include an auxiliary instrument configured to pass through the tubular locking shaft in alignment with a proximal-distal axis of the open recess formed in the implant. The auxiliary instrument can be at least one of a rod reducer and a set screw reducer.

In some embodiments, an implant can include an implant body defining a locking interface in a unilateral portion of the implant body. A proximal-distal axis of the locking interface can be laterally offset from a proximal-distal axis of an open recess formed in the implant. The locking interface can include a top surface of the unilateral portion of the implant, at least two spaced apart grooves formed in an outer surface of the unilateral portion of the implant, and a surface protrusion extending from the outer surface of the unilateral portion of the implant between the at least two spaced apart grooves. The implant can be a bone anchor or a rod-to-rod connector.

In some embodiments, a method of a securing an implant to a surgical instrument can include aligning a unilateral locking mechanism of the surgical instrument with a unilateral portion of the implant, inserting the unilateral locking mechanism onto the unilateral portion of the implant until a distal-facing bearing surface of the unilateral locking mechanism engages a counterpart proximal-facing bearing surface of the unilateral portion of the implant, and controlling movement of a clasp of the unilateral locking mechanism such that a bearing surface of the clasp engages a counterpart bearing surface of the unilateral portion of the implant. The method can further include inserting a rod into the implant while the implant is secured to the instrument.

Inserting the unilateral locking mechanism onto the unilateral portion of the implant can include sliding at least a pair of lateral-facing bearing surfaces along at least a pair of lateral-facing grooves defined along the unilateral portion of the implant. Where the distal-facing bearing surface of the unilateral locking mechanism includes a distal-facing bearing surface formed on one or more prongs extending from a distal end of the unilateral locking mechanism, inserting the unilateral locking mechanism onto the unilateral portion of the implant can include sliding the one or more prongs along one or more lateral-facing grooves defined along the unilateral portion of the implant until the distal-facing surface of the one or more prongs contacts a distal edge of the one or more lateral-facing grooves.

Controlling the movement of the clasp can include actuating a control shaft coupled to the clasp such that movements of the control shaft in a first direction cause a proximal-facing bearing surface of the clasp to engage a counterpart distal-facing bearing surface of the unilateral portion of the implant. Controlling the movement of the clasp can include sliding a locking sleeve over an outer portion of the clasp such that a surface protrusion formed on an inner portion of the clasp engages a counterpart groove formed in the unilateral portion of the implant.

BRIEF DESCRIPTION OF THE DRAWINGS

The accompanying drawings, which are incorporated herein and constitute part of this specification, illustrate exemplary embodiments, and together with the general description given above and the detailed description given below, serve to explain the features of the various embodiments.

FIGS. 1A and 1B are schematic diagrams illustrating perspective and exploded views of a surgical instrument that includes a unilateral locking mechanism according to a first embodiment.

FIGS. 6A and 6B are schematic diagrams illustrating perspective and exploded views of a surgical instrument that includes a unilateral locking mechanism according to a second embodiment.

FIG. 7 is a schematic diagram illustrating the clasp and clasp guide of the locking mechanism according to the second embodiment.

FIGS. 8A and 8B are schematic diagrams illustrating perspective and exploded views of a surgical instrument that includes a unilateral locking mechanism according to a third embodiment.

FIGS. 11A and 11B are schematic diagrams illustrating perspective and exploded views of a surgical instrument having a unilateral locking mechanism according to a fourth embodiment.

FIGS. 12A and 12B are schematic diagrams illustrating components of the partial tubular locking shaft segment according to the fourth embodiment.

FIGS. 14A and 14B are schematic diagrams illustrating perspective and exploded views of a surgical instrument that includes a unilateral locking mechanism according to a fifth embodiment.

FIGS. 17A and 17B are schematic diagrams illustrating a locking operation between the unilateral locking mechanism according to the fifth embodiment.

DETAILED DESCRIPTION

Various embodiments will be described in detail with reference to the accompanying drawings. Wherever possible, the same reference numbers will be used throughout the drawings to refer to the same or like parts. References made to particular examples and implementations are for illustrative purposes, and are not intended to limit the scope of the claims.

Various embodiments are disclosed herein of a surgical instrument that includes a unilateral locking mechanism arranged at a distal end of the instrument for rigidly holding an implant, such as a rod-to-rod connector or bone anchor. The locking mechanism may be configured to lock onto one end of an implant (i.e., a unilateral portion). For example, the locking mechanism may be configured to lock onto a unilateral portion of the implant such that access to an open recess or slot (e.g., for receiving a rod or a set screw) is not blocked. The locking mechanism may be configured to lock onto the unilateral portion of the implant by engaging a counterpart locking interface defined therein. By engaging the instrument's locking mechanism with the implant's counterpart locking interface, sufficient clamping force may be applied by the locking mechanism to resist multi-directional forces exerted on the implant during a surgical procedure. In some embodiments, the surgical instrument may be a stand-alone unilateral implant holder. In some embodiments, the surgical instrument may be configured to perform a surgical task while concurrently holding the implant in place using a unilateral locking mechanism. For example, the surgical instrument may include or be used with a rod reducer, a set screw inserter, or the like.

Figure 1B:
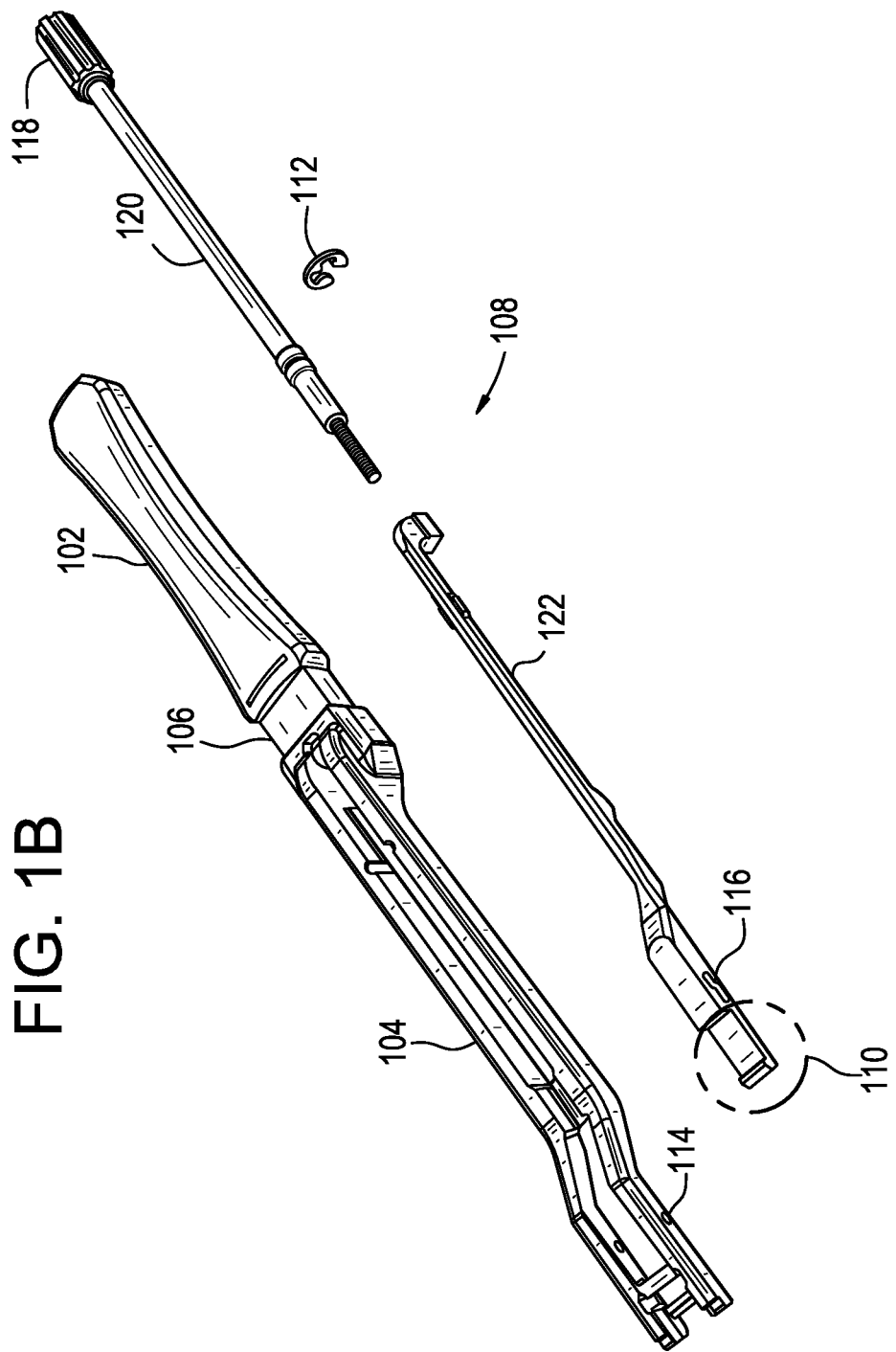

FIGS. 1A and 1B are schematic diagrams illustrating perspective and exploded views of a surgical instrument that includes a unilateral locking mechanism according to a first embodiment. As shown, the instrument 100 may include a proximal handle 102 and a distal unilateral locking mechanism 104. The handle 102 may include at least one handle segment 106 configured to attach an auxiliary instrument (e.g., a rod reducer, a set screw reducer, or the like). The locking mechanism 104 may include an elongated body having a proximal end coupled to the handle 102 and a distal end defining multiple locking elements configured to engage a unilateral portion of an implant. The locking elements may be configured to engage the unilateral portion of the implant such that the locking elements are laterally offset from a proximal-distal axis of an open recess for receiving, e.g., a screw and/or a rod. At least one of the locking elements may include a clasp 110 extending from a control shaft 108. The control shaft 108 may be moveably coupled to the handle 102 by a retaining clip 112 and to the locking mechanism 104 by a pin 114 and slot 116 interface. The control shaft 108 may be configured to move in response to rotation of a knob 118 or other type of actuation control, thereby causing the clasp 110 to lock or unlock the implant. The control shaft 108 may include a proximal shaft portion 120 threadably coupled to a distal shaft portion 122. As described in more detail below, the locking elements may be configured to contact, mate, interlock, or otherwise engage counterpart locking elements defined in a unilateral locking interface of an implant.

Figure 2:
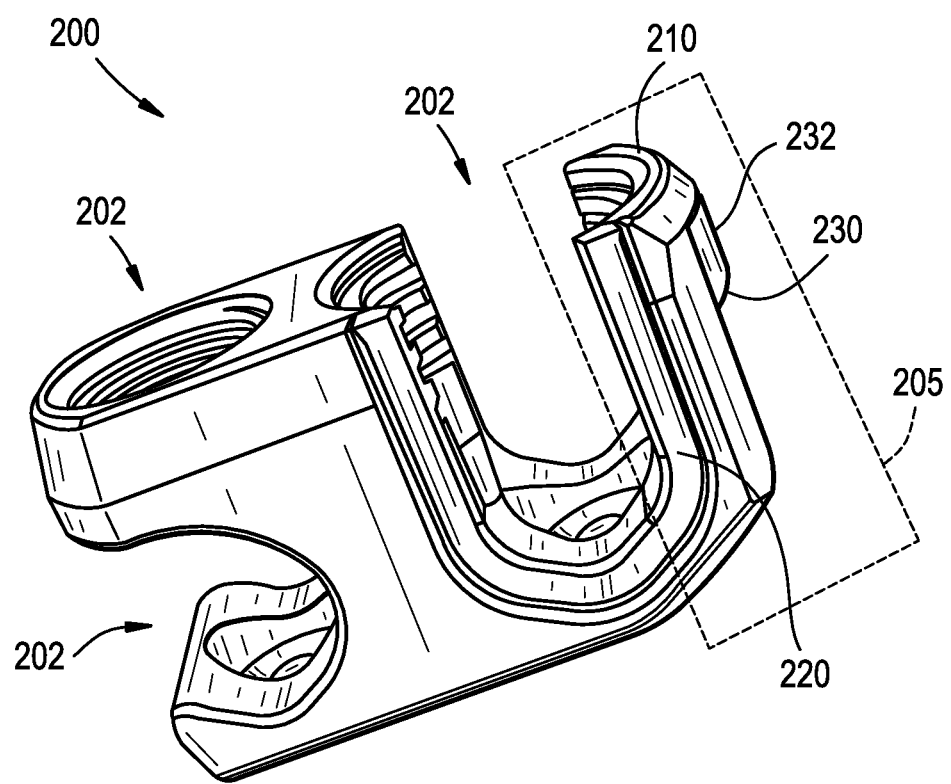
FIG. 2 is a schematic diagram illustrating various counterpart locking elements of a unilateral locking interface defined in a unilateral portion of an implant according to an embodiment.

FIG. 2 is a schematic diagram illustrating various counterpart locking elements of a unilateral locking interface defined in a unilateral portion of an implant according to an embodiment. Although the illustrated implant 200 is a rod-to-rod connector, the counterpart unilateral locking interface may be integrated into other types of connectors and bone anchors. As shown, the implant 200 may include one or more open recesses 202 formed in the body of the implant (e.g., for receiving a rod and/or a set screw). A unilateral portion of an implant may be a portion of the implant that is located towards one end of the implant. For example, the unilateral portion 205 may correspond to an end portion of the implant 200 opposing the open recesses 202. By defining the locking interface towards one side of the open recesses 202, the recesses may continue to be accessible (e.g., not blocked) after the instrument's locking mechanism 106 is engaged in a locked configuration.

As shown, the locking interface of the implant 200 may include a top or proximal-facing bearing surface 210, laterally-facing grooves 220, and a distal-facing bearing surface 230. Each of these counterpart locking elements may be configured to contact, mate, interlock, or otherwise engage the locking elements of the instrument's locking mechanism 104, thereby constraining movement of the implant in all directions. For example, as shown in FIG. 2, the top or proximal-facing bearing surface 210 may correspond to a top surface of the implant 200 which may partially surround the upper edge of an open recess 202. The pair of laterally-facing grooves 220 may correspond to a pair of vertical grooves formed in a sidewall of the connector adjacent to the open recess 202. The vertical grooves 220 may intersect with the recess 202, as shown in FIG. 2, or may be spaced a distance apart from the recess. The distal-facing bearing surface 230 may be formed on a lateral locking protrusion 232 at the back surface of the implant and extend transversely between the pair of vertical grooves 220. In some embodiments, the implant may also include a horizontal groove or notch (not shown) formed along a proximal end of the unilateral portion below the top or proximal-facing bearing surface.

Figure 3A:
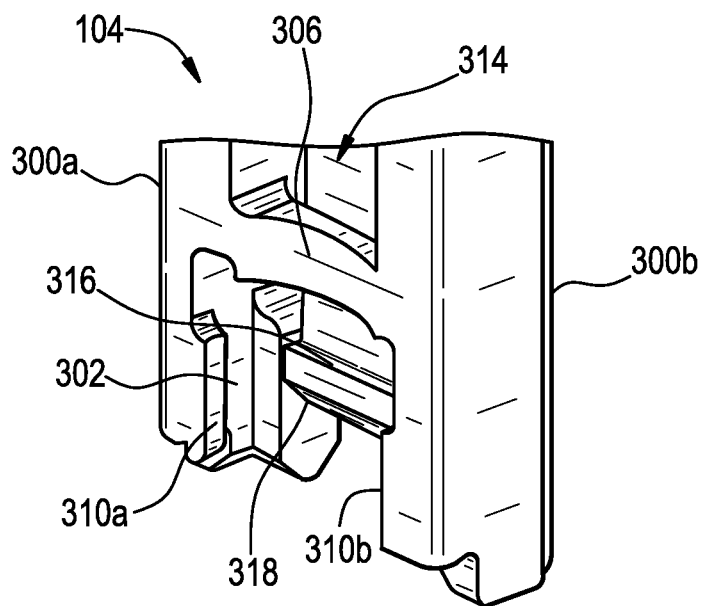
FIGS. 3A and 3B are schematic diagrams illustrating various locking elements of a unilateral locking mechanism according to the first embodiment.
Figure 3B:
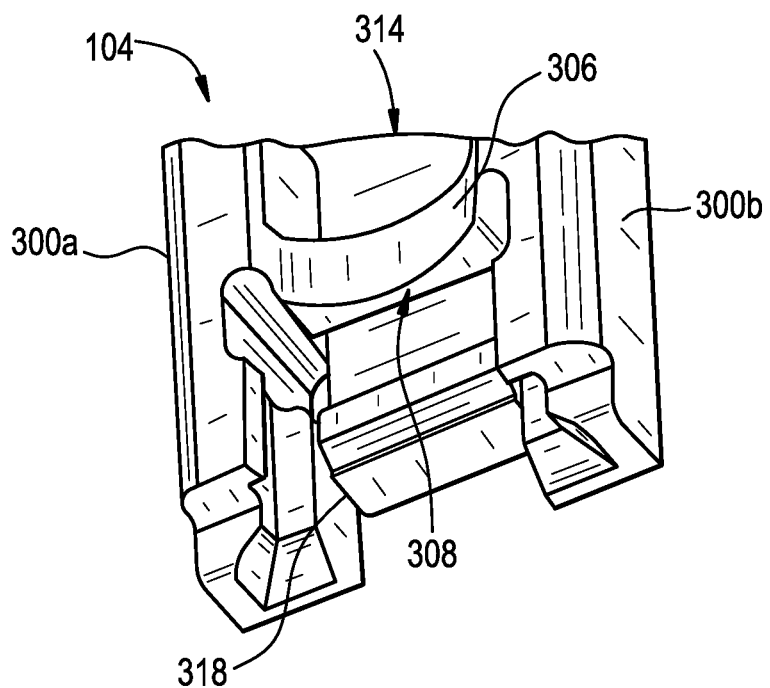

FIGS. 3A and 3B are schematic diagrams illustrating various locking elements of a unilateral locking mechanism according to the first embodiment. As shown, the locking mechanism 106 may include a pair of parallel arms 300a and 300b (collectively 300). The spacing and dimensions of the arms 300 may be configured to form an implant-receiving pocket 302 between opposing faces of the arms 300. The pocket 302 may be configured to accommodate a width and a depth of the unilateral portion of the implant (e.g., 205 of FIG. 2).

The locking mechanism 106 may include a horizontal stop beam 306 that extends transversely between opposing faces of the arms 300. A height of the stop beam 306 relative to the distal end of the arms 300 may be configured to accommodate, or at least partially accommodate, the height of the unilateral portion of the implant. The stop beam 306 may have a distal-facing bearing surface 308 configured to contact the top or proximal bearing surface of the implant's locking interface (e.g., 210 of FIG. 2), thereby constraining longitudinal movements of the implant in a proximal direction (e.g., upward movements). The stop beam 306 may have a shape that conforms to the shape of the top bearing surface of the implant's locking interface (e.g., 210 of FIG. 2). For example, where the implant's top bearing surface forms an outer edge of an open recess for receiving a rod or a set screw, the forward and distal faces of the stop beam 306 may be shaped such that the stop beam does not block or otherwise interfere with the open recess of the implant.

The locking mechanism 106 may include a pair of opposing insertion tabs 310a and 310b (collectively 310) that protrude longitudinally along opposing faces of the arms 300 at or adjacent to the front of the pocket 302. The insertion tabs 310 may have lateral-facing bearing surfaces configured to mate and slide along lateral-facing counterpart grooves formed in the unilateral portion of the implant (e.g., grooves 220 of FIG. 2), thereby constraining lateral movements of the implant (e.g., side-to-side and front-to-back movements).

The locking mechanism 106 may include a retractable clasp 314 disposed between the opposing faces of the arms 300 at or adjacent to the back of the pocket 302. The clasp 314 may include a generally rectangular-shaped body forming a lateral locking protrusion 318 that extends along a width of the distal end of the clasp 314. A proximal-facing bearing surface may be formed on the lateral locking protrusion 318 and configured to interlock with a counterpart distal-facing bearing surface formed in the unilateral portion of the implant (e.g., 230 of FIG. 2), thereby constraining longitudinal movements of the implant in a distal direction (e.g., downward movements).

The clasp 314 may be configured to move upward and inward towards a locked configuration in which the clasp's proximal-facing bearing surface 316 is forced against the distal-facing bearing surface of the implant's locking interface (e.g., 230 of FIG. 2). The clasp 314 may be configured to move downward and outward away from the locked configuration towards an unlocked configuration in which the clasp's proximal-facing bearing surface 316 is disengaged from the distal-facing bearing surface of the implant's locking interface.

Figure 4A:
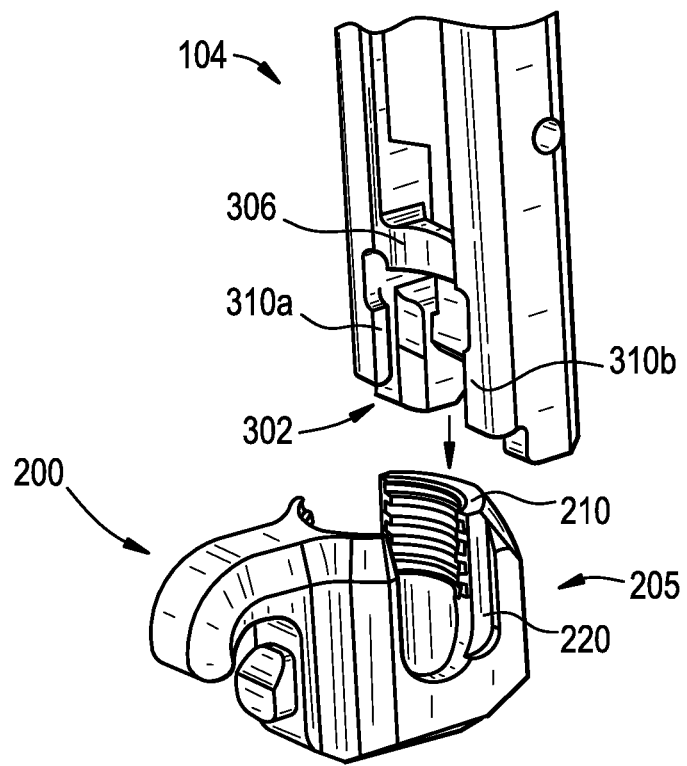
FIGS. 4A through 4D are schematic diagrams illustrating a locking operation of the unilateral locking mechanism according to the first embodiment.
Figure 4B:
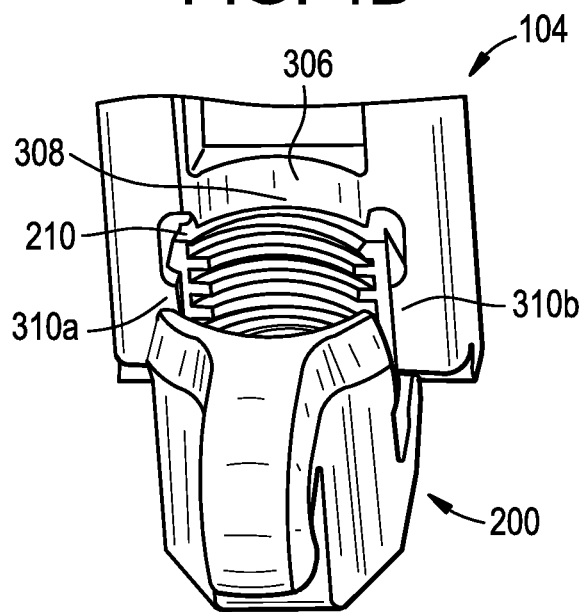

FIGS. 4A through 4D are schematic diagrams illustrating a locking operation between the unilateral locking mechanism according to the first embodiment. As shown in FIG. 4A, the locking mechanism 104 may be initially positioned over a proximal end of an implant 200 such that the implant-receiving pocket 302 is aligned with the unilateral portion 205 of the implant. As the locking mechanism 104 is inserted distally towards the implant 200, the insertion tabs 310 of the locking mechanism may slide longitudinally along the lateral-facing grooves 220 of the locking interface, thereby guiding the unilateral portion 205 of the implant 200 proximally into the pocket 302. As shown in FIG. 4B, the insertion tabs 310 may continue to slide along the grooves until the distal-facing bearing surface 308 of the stop beam 306 contacts or abuts the top or proximal bearing surface 210 of the implant's locking interface.

Figure 4C:
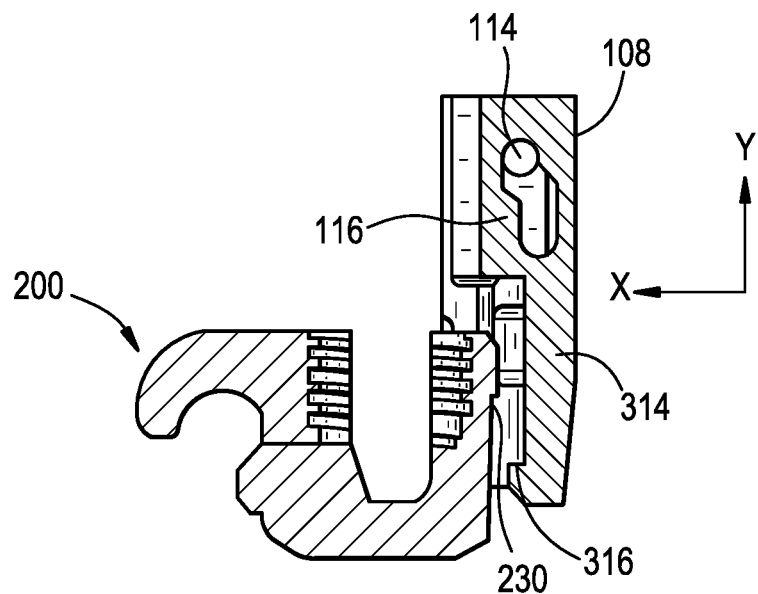
Figure 4D:
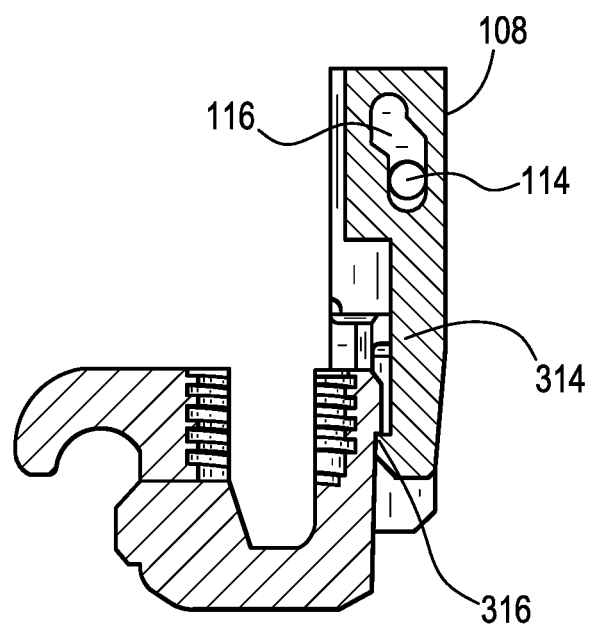

Once the implant's top bearing surface 210 contacts or abuts the stop beam 306, the clasp 314 may be engaged to lock the implant in place. As shown in FIGS. 4C and 4D, a pin 114 and slot 116 interface may be used to control the movement of the clasp 314 from an unlocked configuration to a locked configuration relative to the implant. A pin 114 may be configured to protrude from at least one of the opposing faces of the arms 300 through a slot 116 formed in the control shaft 108. The slot 116 may include a ramped portion that extends obliquely with respect to the longitudinal axis of the clasp 314. Accordingly, movement of the pin 114 along the slot 116 can be effective to move or flex the clasp 314 radially-inward or radially-outward relative to the arms 300. Other configurations of the pin and slot interface may be employed to control the movement of the clasp 314.

As shown in FIG. 4C, the clasp 314 may start from an unlocked configuration in which the clasp's proximal-facing bearing surface 316 is disengaged from the implant 200 at a position located down and away relative to the implant in the pocket 302. As the control shaft 108 moves in a proximal direction, the clasp 314 may traverse a proximal path guided by the geometry of the slot interface 116.

As shown in FIG. 4D, the clasp 314 may be pulled upward (e.g., proximally along the y-axis) and inward (e.g., laterally along the x-axis) towards a locked configuration, thereby forcing the clasp's proximal-facing bearing surface 316 against a distal-facing bearing surface 230 of the implant 200. As previously discussed, the distal-facing bearing surface 230 may be formed on a lateral locking protrusion (e.g., 232 of FIG. 2). In this locked configuration, the implant 200 may be captured within the pocket 302 at one end (e.g., the unilateral portion 205 of FIG. 2) and constrained from longitudinal movement (e.g., upward and downward movement along a y-axis) and lateral movements (e.g., side-to-side and forward-to-back movements in a x-z plane). To release the implant from the locking mechanism 104, the clasp 314 may traverse a distal path guided by the geometry of the slot interface 116 towards the unlocked configuration in response to the control shaft 108 moving in a distal direction.

Figure 5A:
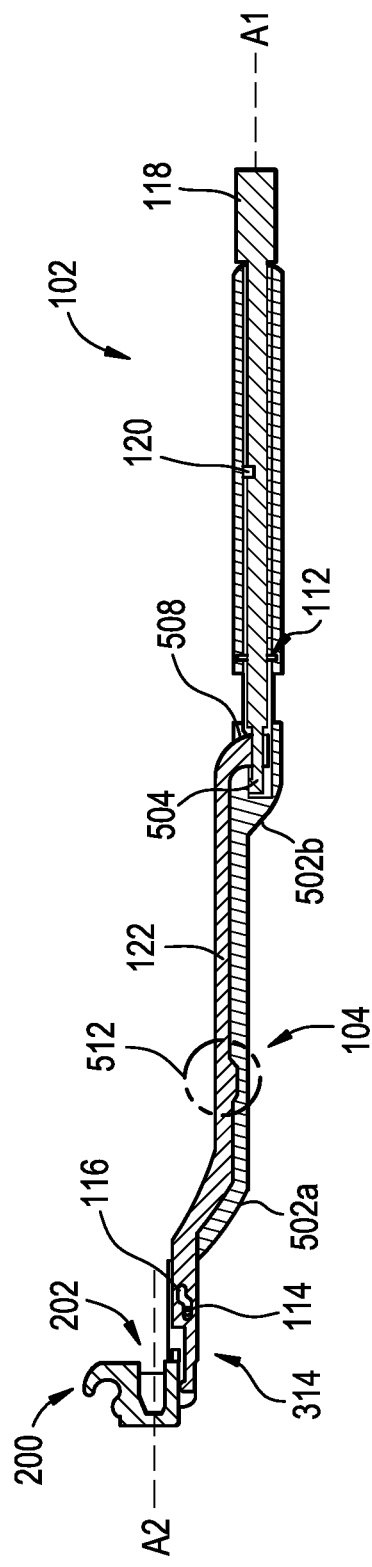
FIGS. 5A and 5B are schematic diagrams illustrating the operation of a control shaft 108 according to the first embodiment.
Figure 5B:
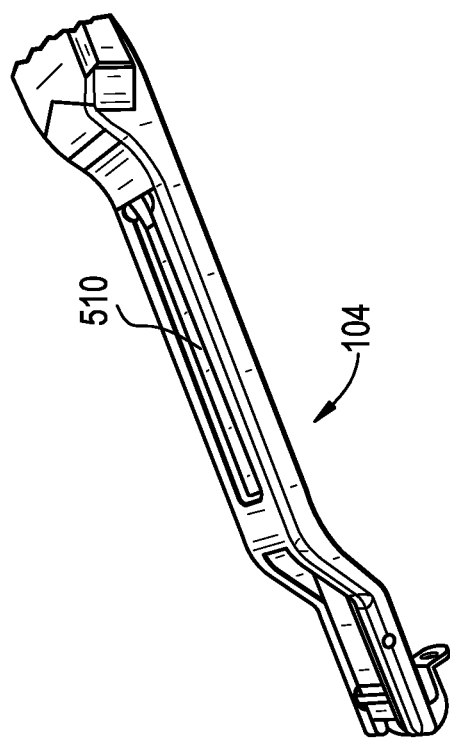

FIGS. 5A and 5B are schematic diagrams illustrating the operation of a control shaft 108 according to the first embodiment. As shown, the control shaft may be configured to have a proximal shaft portion 120 disposed in the handle 102 and a distal shaft portion 122 disposed in the elongated body of the unilateral locking mechanism 104. The elongated body of the unilateral locking mechanism 104 may be shaped to include one or more angular body segments 502a and 502b (collectively angular segments 502) such that the body segments 502 are angled to offset a longitudinal axis A1 of the handle 102 from a proximal-distal axis A2 of an open recess (e.g., 202 of FIG. 2) defined in the body of the implant (e.g., 200 of FIG. 2).

The proximal shaft portion 120 may have a knob 118 coupled to a proximal end and a threaded portion 502 at a distal end. The proximal shaft portion 120 may disposed within a hollow interior of the handle portion 102 by a retaining clip 112 and configured to rotate about the longitudinal axis of the handle portion in response to turning of the knob 118. A threaded portion 504 of the proximal shaft portion 120 may be threadably coupled to a proximal nut 508 of the distal shaft portion 122.

By threadably coupling the proximal and distal shaft portions, rotations of the proximal shaft portion 120 may induce translational movements of the distal shaft portion 122. For example, rotations of the proximal shaft portion 120 in one direction may cause the distal shaft portion 122 to move proximally away from the locking mechanism 104, such that the clasp 314 moves towards a locked configuration to engage the implant 200. Conversely, rotations of the proximal shaft portion 120 in an opposite direction may cause the distal shaft portion 122 to move distally towards the locking mechanism 104, such that the clasp 314 moves towards an unlocked configuration to disengage the implant 200.

A pin 114 and slot 116 interface may be configured to guide the translational movements of the distal shaft portion 122 between the locked and unlocked configurations. The pin 114 may be biased against an edge of the slot 116 using a spring-loaded biasing element 510 formed in the handle portion 104 of the elongated body. The spring-loaded biasing element 510 may be configured to exert a force on a surface protrusion 512 of the distal shaft portion 122 (e.g., a tooth), such that the exerted force urges the pin 114 to slide along an edge of the slot 116 during translation of the distal shaft portion 122.

Figure 6B:
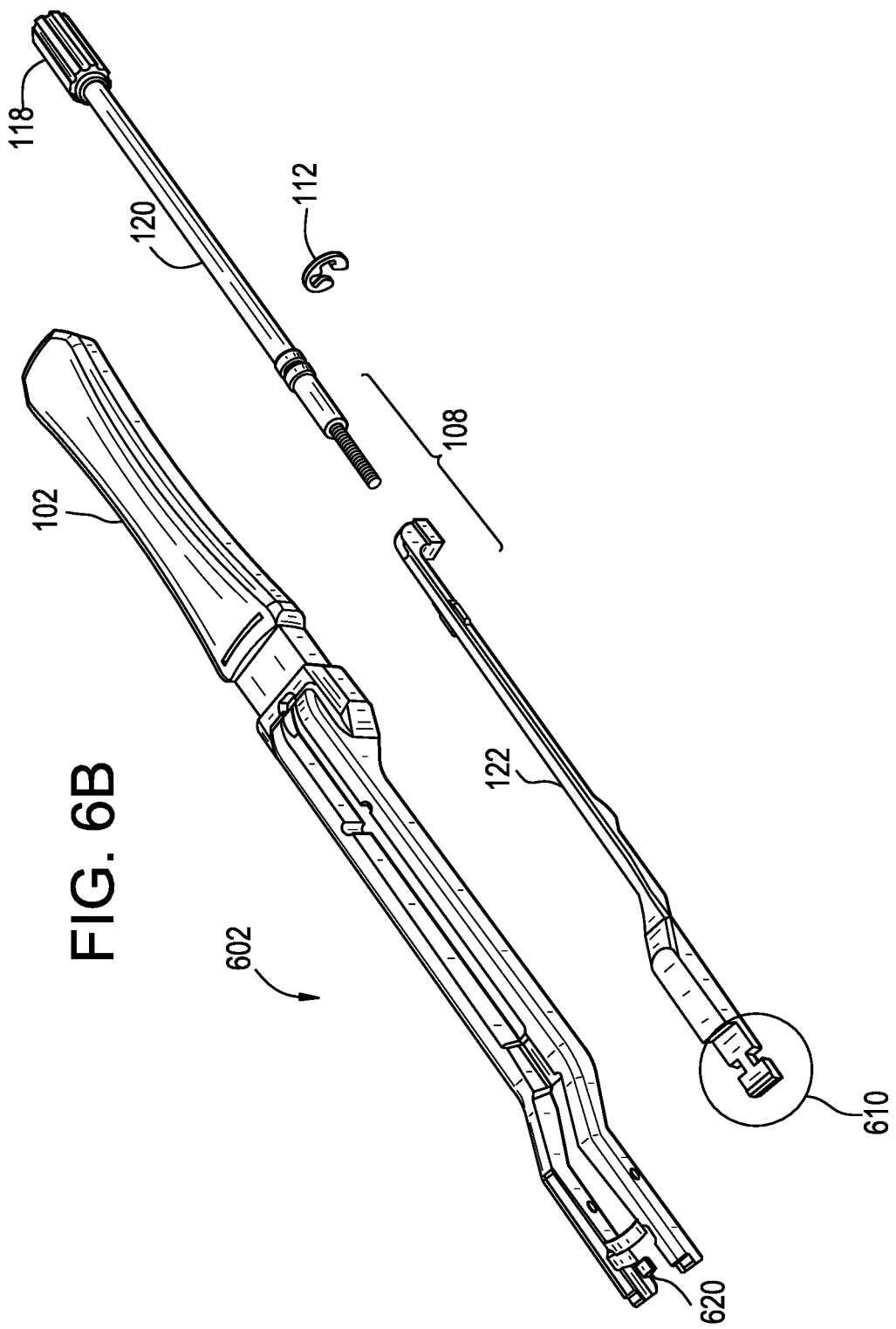

FIGS. 6A and 6B are schematic diagrams illustrating perspective and exploded views of a surgical instrument that includes a unilateral locking mechanism according to a second embodiment. As shown, the instrument 600 may include a proximal handle 102 and a distal unilateral locking mechanism 602. The handle 102 may include at least one handle segment 106 configured to attach an auxiliary instrument (e.g., a rod reducer, a set screw reducer, or the like). The locking mechanism 602 may include an elongated body having a proximal end coupled to the handle 102 and a distal end defining multiple locking elements configured to engage a unilateral portion of an implant.

With reference to FIGS. 1A through 6B, the locking elements of the locking mechanism 602 may have a structure and operation similar to the structure and operation of the instrument 100. However, as discussed in more detail below, the locking mechanism 602 may include a clasp 610 and a clasp guide 620 configured with various ramped bearing surfaces. The ramped bearing surfaces of the clasp 610 and the clasp guide 620 may be employed to alleviate the need for a pin and slot interface (e.g., 114 and 116) to control the movements of the clasp between the locked and unlocked configurations. The clasp 610 may extend from a control shaft 108 and the control shaft may be moveably coupled to the handle 102 by a retaining clip 112. The control shaft 108 may be configured to move in response to rotation of a knob 118 or other type of actuation control, thereby causing the clasp 610 to lock or unlock the implant. The control shaft 108 may include a proximal shaft portion 120 threadably coupled to a distal shaft portion 122.

FIG. 7 is a schematic diagram illustrating the clasp and clasp guide of the locking mechanism according to the second embodiment. As shown, the clasp guide 620 may include a pair of clasp guide structures 702a and 702b (collectively 702) protruding between the opposing faces of the arms 300 at or adjacent to the back of the pocket 302. A narrow spatial region 704 may be formed between the opposing faces of the guide structures. The clasp guide structures 702 may be configured to have a cross-sectional shape of a rhombus or other parallelogram and oriented to form a pair of proximal-facing ramped bearing surfaces 708a and 708b (collectively 708) and a pair of distal-facing ramped bearing surfaces 710a and 710b (collectively 710). The distal-facing ramped bearing surfaces 710 may be obliquely angled to guide the clasp 610 upward and inward towards the locked configuration in response to proximal movements of the control shaft. The proximal-facing ramped bearing surfaces 708 may be obliquely angled to guide the clasp 610 downward and outward away from the locked configuration.

The clasp 610 may have a substantially rectangular body coupled to a control shaft 108 at a proximal end and a lateral locking protrusion 714 having a proximal-facing bearing surface 716 configured to engage the implant formed along the width of the distal end. The clasp 610 may further include a counterpart guide structure formed between the proximal and distal ends of the clasp. As shown, the counterpart guide structure may include a narrow body region 718 formed in the body of the clasp 610 between a proximal portion and a distal portion of the clasp. The narrow body region 718 may be configured to have a reduced width less than respective widths of the proximal portion and the distal portion of the clasp. The reduced width of the narrow body region 718 may be configured to pass through the width of the narrow spatial region 704 formed between the opposing faces of the guide structures 702. The counterpart guide structure may further include a pair of counterpart distal-facing ramped bearing surfaces 720a and 720b (collectively 720) extending laterally at a proximal end of the narrow body region 718 and a pair of counterpart proximal-facing ramped bearing surfaces 722a and 722b (collectively 722) extending laterally at a distal end of the narrow body region 718.

In operation, the clasp 610 may start from an unlocked configuration in which the clasp's proximal-facing bearing surface 716 is disengaged from the implant at a position located down and away relative to the implant in the pocket. As the control shaft 108 is moved in a proximal direction, the clasp 610 may be pulled upward such that the clasp's counterpart proximal-facing ramped bearing surfaces 722 begin to slide against the distal-facing ramped bearing surfaces 710 of the guide structures 702. The clasp 610 may continue to slide along the guide structures 702 until reaching the locked configuration at which the clasp's proximal-facing bearing surface 716 of the lateral locking protrusion 714 is forced against a distal-facing bearing surface of the implant (e.g., 230 of FIG. 2). The distal-facing ramped bearing surfaces 710 of the guide structures may be configured at an oblique angle, such that the clasp 610 may be pulled upward (e.g., proximally along the y-axis) and inward (e.g., laterally along the x-axis) towards the locked configuration.

As the control shaft 108 is moved a distal direction, the clasp 610 may be pushed downward, such that the clasp's counterpart distal-facing ramped bearing surfaces 720 begins to slide against the proximal-facing ramped bearing surfaces 708 of the guide structures 702. The clasp 610 may continue to slide along the guide structures 702 until reaching the unlocked configuration at which the clasp's proximal-facing bearing surface 716 of the lateral locking protrusion 714 is released from a distal-facing bearing surface of the implant (e.g., 230 of FIG. 2). The proximal-facing ramped bearing surfaces 708 of the guide structures may be configured at an oblique angle, such that the clasp 610 may be slid downward (e.g., distally along the y-axis) and outward (e.g., laterally along the x-axis) away from the locked configuration.

Figure 8B:
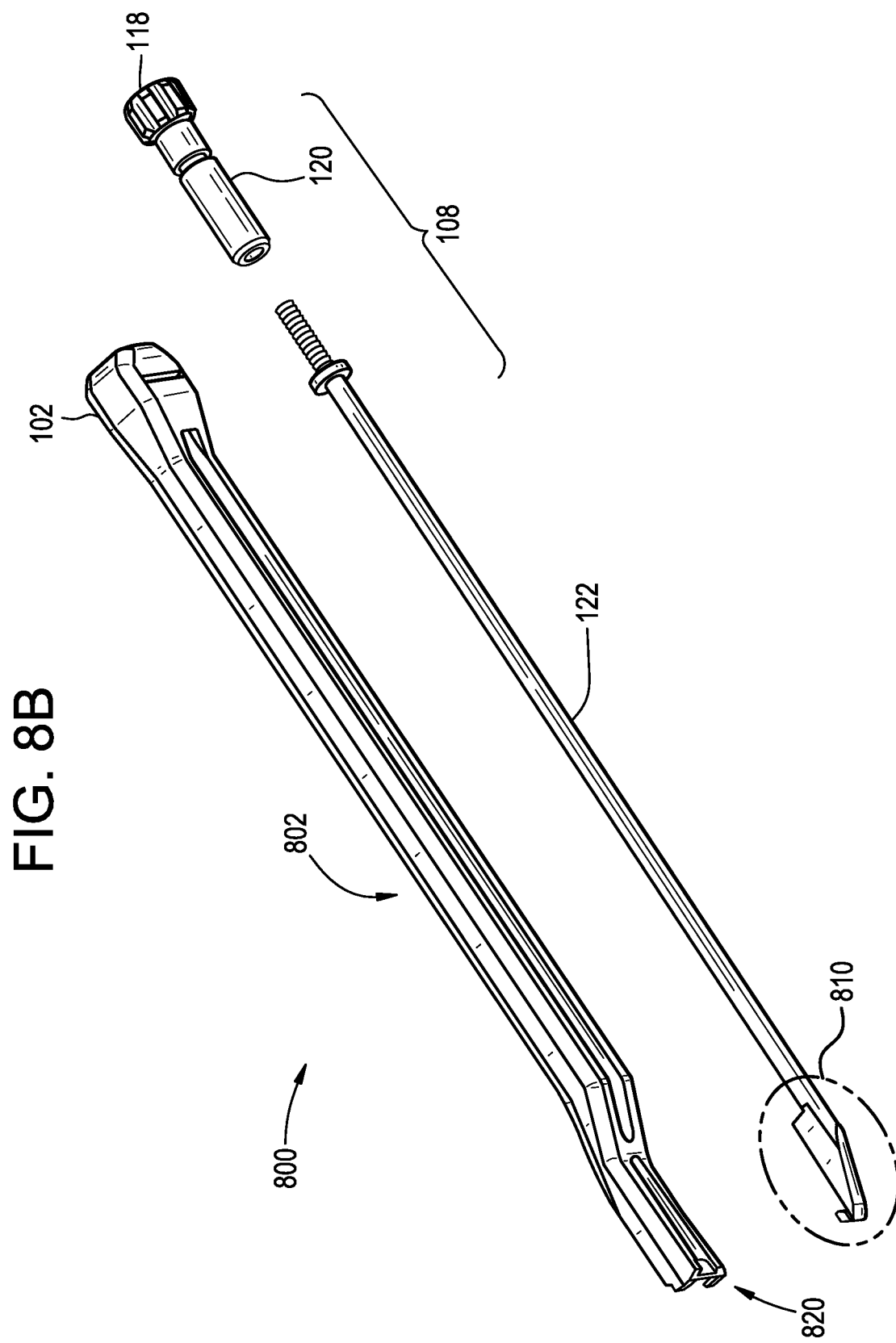

FIGS. 8A and 8B are schematic diagrams illustrating perspective and exploded views of a surgical instrument that includes a unilateral locking mechanism according to a third embodiment. As shown, the instrument 800 may include a proximal handle 102 and a distal unilateral locking mechanism 802. The locking mechanism 802 may include an elongated body having a proximal end coupled to the handle 102 and a distal end defining multiple locking elements configured to engage a unilateral portion of an implant.

With reference to FIGS. 1A through 8B, the locking elements of the locking mechanism 802 may have a structure and operation similar to the structure and operation of the instrument 100. However, as discussed in more detail below, the locking mechanism 802 may include a modified clasp 810 and a clasp guide 820 configured with various ramped and vertical bearing surfaces. The ramped and vertical bearing surfaces of the clasp 810 and the clasp guide 820 may be employed to alleviate the need for a pin and slot interface (e.g., 114 and 116) to control the movements of the clasp between the locked and unlocked configurations. The clasp 810 may extend from a control shaft 108 and the control shaft may be moveably coupled to the handle 102. The control shaft 108 may be configured to move in response to rotation of a knob 118 or other type of actuation control, thereby causing the clasp 810 to lock or unlock the implant. The control shaft 108 may include a proximal shaft portion 120 threadably coupled to a distal shaft portion 122.

Figure 9:
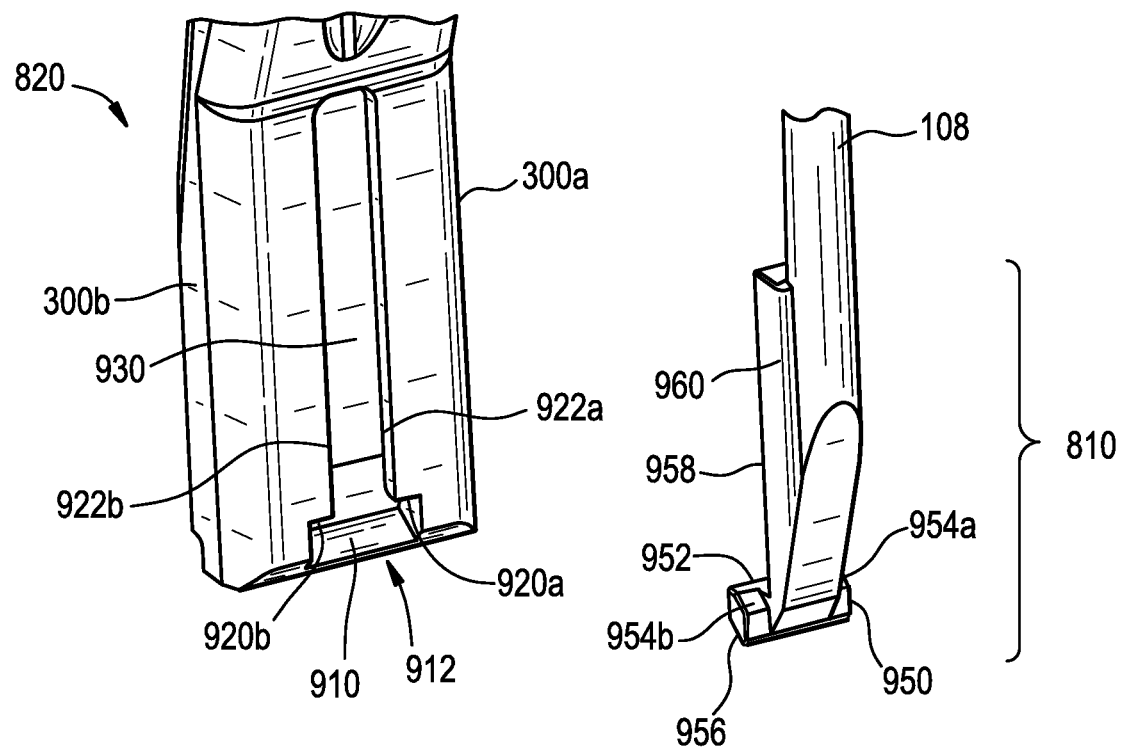
FIG. 9 is a schematic diagram illustrating the clasp and clasp guide of the locking mechanism according to the third embodiment.

FIG. 9 is a schematic diagram illustrating the clasp 810 and clasp guide 820 of the locking mechanism 802 according to the third embodiment. As shown, the clasp guide 820 may include a proximal-facing ramped bearing surface 910, at least a pair of distal-facing ramped bearing surfaces 920a and 920b (collectively 920), and a lateral-facing vertical bearing structure 930. The guide's proximal-facing ramped bearing surface 910 may be formed on a lateral beam 912 that extends transversely between the distal ends of the arms 300. The guide's proximal-facing ramped bearing surface 910 may be obliquely angled to guide lateral movement of the clasp 810 away from a locked configuration towards an unlocked configuration (e.g., outward along the x-axis) in response to distal movements of the control shaft 108.

Proximal to the lateral beam 912, the guide's distal-facing ramped bearing surfaces 920 may be formed on the distal ends of laterally opposing guide rails 922a and 922b (collectively 922) that extend longitudinally along the arms 300 of the locking mechanism towards a proximal end. The guide's distal-facing ramped bearing surfaces 922 may be obliquely angled to guide the lateral movement of the clasp 810 away from an unlocked configuration towards the locked configuration (e.g., inward along the x-axis) in response to proximal movements of the control shaft 108. The guide's vertical bearing surface 930 may extend transversely between the opposing guide rails 922 forming an elongated recess. The guide's distal-facing vertical bearing surface 930 may be configured to guide longitudinal movements of the clasp 810 between the locked and unlocked configurations (e.g., along the y-axis) in response to proximal or distal movements of the control shaft 108.

The clasp 810 may have an elongated body with a proximal end coupled to a control shaft 108 and a distal end forming a lateral locking protrusion 950. The locking protrusion 950 of the clasp may have a proximally-facing bearing surface 952 formed thereon for engaging an implant (e.g., 200 of FIG. 2) in a locked configuration. The clasp 810 may be configured to have a counterpart guide structure that includes at least a pair of proximal-facing ramped bearing surfaces 954a and 954b (collectively 954), a distal-facing ramped bearing surface 956, and a lateral-facing vertical bearing surface 958.

The lateral-facing vertical bearing surface 958 of the clasp's guide structure may be formed on a substantially rectangular portion 960 that extends longitudinally between the proximal and distal ends of the clasp 810. The proximal-facing ramped bearing surfaces 954 of the clasp's guide structure may be formed on a proximal end of the lateral locking protrusion 950 on opposite sides of the vertical bearing surface 958. The distal-facing ramped bearing surface 956 of the clasp's guide structure may be formed along the width of the distal end of the lateral locking protrusion 950.

Figure 10A:
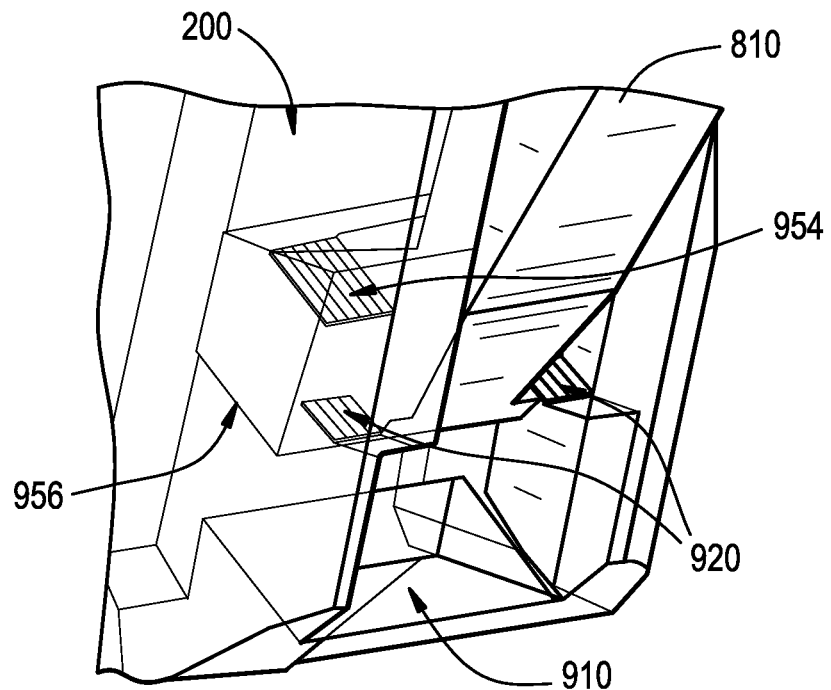
FIGS. 10A through 10D are schematic diagrams illustrating an operation of the clasp and clasp guide of the locking mechanism according to the third embodiment.
Figure 10B:
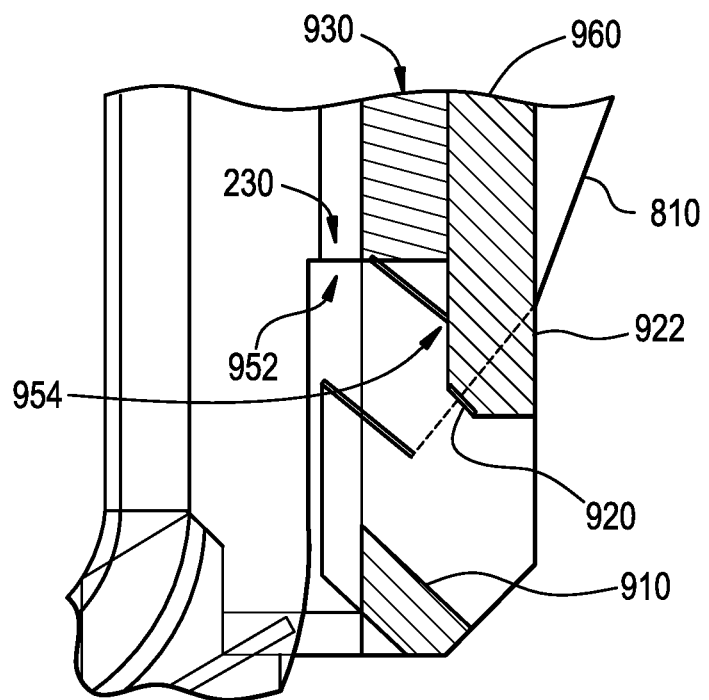
Figure 10C:
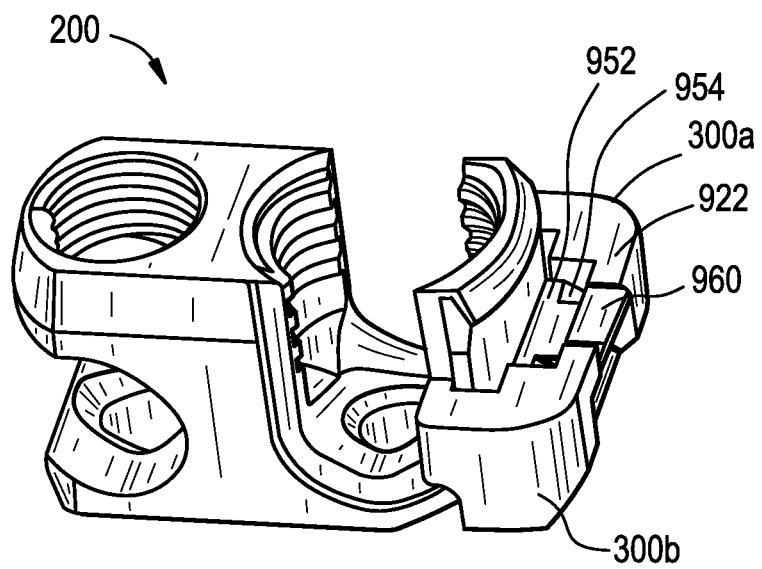
Figure 10D:
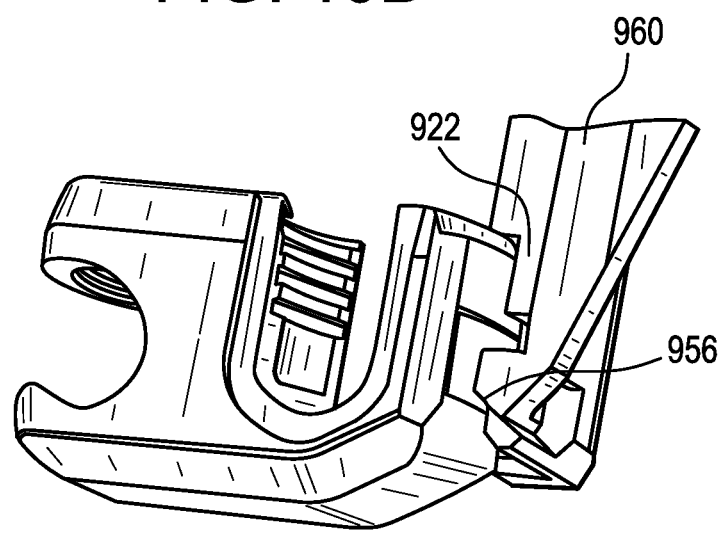

FIGS. 10A and 10D are schematic diagrams illustrating an operation of the clasp and clasp guide of the locking mechanism according to the third embodiment. The clasp 810 may initially start from an unlocked configuration in which the proximal-facing bearing surface 952 along the clasp's lateral locking protrusion 950 is disengaged from the implant 200 at a position located down and away relative to the implant 200. As the control shaft 108 is moved in a proximal direction, the clasp 810 may be pulled upward such that the clasp's proximal-facing ramped bearing surfaces 954 may begin to slide against the guide's distal-facing ramped bearing surfaces 920 formed on at the distal ends of the guide rails 922. The distal-facing ramped bearing surfaces 920 of the guide structures may be configured at an oblique angle, such that the clasp 810 may be pulled upward (e.g., proximally along the y-axis) and inward (e.g., laterally along the x-axis) towards the locked configuration. The clasp 810 may continue to slide along the guide's distal-facing ramped bearing surfaces 920 until the end of the clasp's proximal-facing ramped bearing surfaces 954 is reached. When the end of the clasp's proximal-facing ramped surface 954 is reached, the clasp's vertical bearing surface 958 may be flush or at least in contact with the guide's vertical bearing surface 930. As the control shaft continues to move in the proximal direction, the clasp's vertical bearing surface 958 slides proximally along the guide's vertical bearing surface 930 until reaching the locked configuration at which the clasp's proximal-facing bearing surface 952 is forced against a distal-facing bearing surface of the implant (e.g., 230 of FIG. 2). In the locked configuration, the guide rails 922 can abut an outer back surface of the lateral locking protrusion 950 to prevent the protrusion 950 from moving laterally-outward away from the implant.

As the control shaft 108 is moved in a distal direction, the clasp 810 may be pushed downward, such that the clasp's counterpart distal-facing ramped bearing surface 956 begins to slide against the proximal-facing ramped bearing surface 910 of the lateral beam 912. The clasp 810 may continue to slide along the lateral beam 912 until reaching the unlocked configuration at which the clasp's proximal-facing bearing surface 952 of the lateral locking protrusion 950 is released from a distal-facing bearing surface of the implant (e.g., 230 of FIG. 2).

Figure 11B:
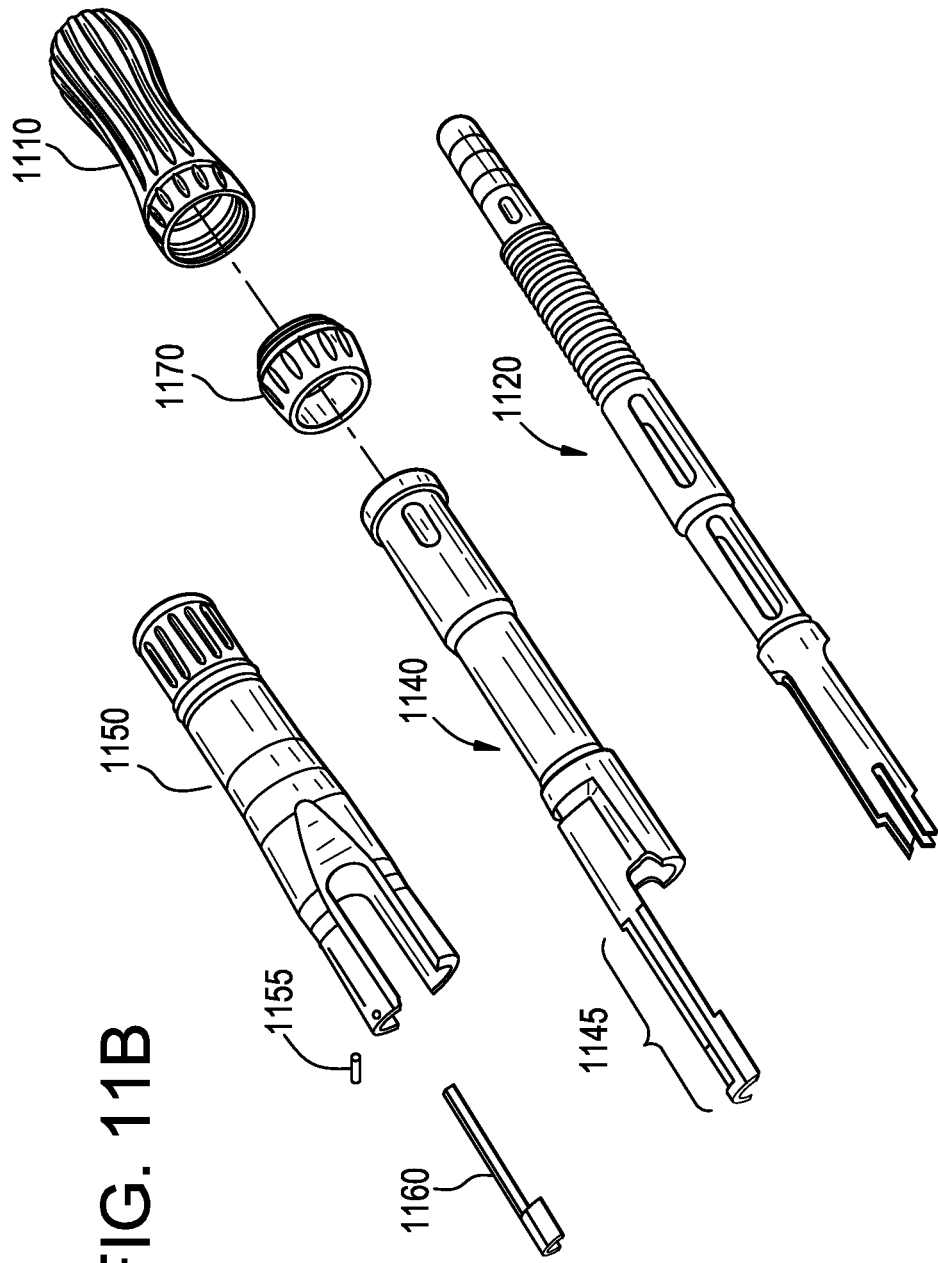

FIGS. 11A and 11B are schematic diagrams illustrating perspective and exploded views of a surgical instrument having a unilateral locking mechanism according to a fourth embodiment. As shown in the illustrated embodiment, a unilateral locking mechanism may integrated into an instrument that is configured to perform another surgical task, such that the surgical task may be performed concurrently while holding the implant in place. Although the instrument as shown is a rod reducer, the unilateral locking mechanism may be integrated into other types of surgical instruments, such as a screw driver, inserter, or the like.

The instrument 1100 may include a handle portion 1110, a rod reducing element 1120, and a unilateral locking mechanism 1130. The unilateral locking mechanism 1130 may include a tubular locking shaft 1140, a partial tubular locking shaft segment 1145, a locking sleeve 1150, a locking pin 1155, a clasp 1160, and a coupling mechanism 1170. The handle portion 1110 may be threadably coupled to a proximal end of the rod reducing element 1120, such that rotations of the handle portion 1110 may cause the rod reducing element 1120 to translate along a longitudinal axis defined therebetween. The handle portion 1110 may be further coupled to a proximal end of the tubular locking shaft 1140, such that the rod reducing element 1120 may extend longitudinally through the hollow interior of the tubular locking shaft 1140. A coupling mechanism 1170 of any type may be used to fix the handle portion 1110 to the proximal end of the tubular locking shaft 1140. The tubular locking shaft 1140 may define a cutaway portion at a distal end to form the partial tubular locking shaft 1145. The partial tubular locking shaft segment 1145 may include multiple locking elements, including the clasp 1160. The multiple locking elements may be configured to contact, mate, interlock, or otherwise engage counterpart locking elements defined in a unilateral locking interface of an implant. For example, as discussed in more detail below, the locking sleeve 1150 may be configured to slide longitudinally over the outer surface of the tubular locking shaft 1140 to engage or disengage the clasp 1160 relative to a unilateral portion of an implant. A locking pin 1155 may be inserted at a distal end of the locking sleeve 1150 perpendicular to a longitudinal axis of the sleeve. Once inserted, the locking pin 1155 may extend transversely across an inner portion of the sleeve, such that the pin may exert a force against the clasp 1160 as the sleeve slides over it.

FIGS. 12A and 12B are schematic diagrams illustrating components of the partial tubular locking shaft segment according to the fourth embodiment. As shown in the illustrated embodiment, the partial tubular locking shaft segment 1145 may have a structure and operation similar to the structure and operation of the instrument 100. For example, the partial tubular locking shaft segment 1145 may define or otherwise have formed thereon a pair of arms 300 configured to form an implant-receiving pocket 302, a stop beam 306 configured to prevent proximal movements of the implant (e.g., upward movements), and a pair of insertion tabs 310 configured to preventing lateral movements of the implant (e.g., side-to-side and front-to-back movements) as previously shown and described with reference to FIGS. 3A, 3B, 4A and 4B.

The partial tubular locking shaft segment 1145 may further include a clasp 1160 having a proximal end portion 1202 and a distal end portion. The proximal end portion 1202 of the clasp 1160 may be fixedly attached to an outer surface of the partial tubular locking shaft segment 1145. The distal end portion may be unattached to the locking shaft segment 1145, forming a free clasp head 1204. The free clasp head 1204 may be aligned with a window 1210 defined in the body of the locking shaft segment 1145 to expose the unilateral portion of an implant situated in the implant-receiving pocket (e.g., the pocket 302 of FIGS. 3A and 3B). The free clasp head 1204 may have dimensions sufficient to fit through the window 1210. The face 1206 of the free clasp head 1204 may define a lateral-facing surface protrusion 1208 configured to engage a counterpart locking element formed in the unilateral portion of the implant, such as a groove or notch. As discussed in more detail below, the free clasp head 1204 may be configured to enter the window 1210 towards the back of the implant-receiving pocket (e.g., 302) in response to the locking sleeve 1150 sliding distally over the free clasp head 1204, such that the locking pin 1155 may urge against the free clasp head 1204. Conversely, the free clasp head 1204 may be configured to exit the window away from the implant-receiving pocket (e.g., 302) in response to the locking sleeve sliding proximally away from the free clasp head 1204.

Figure 13A:
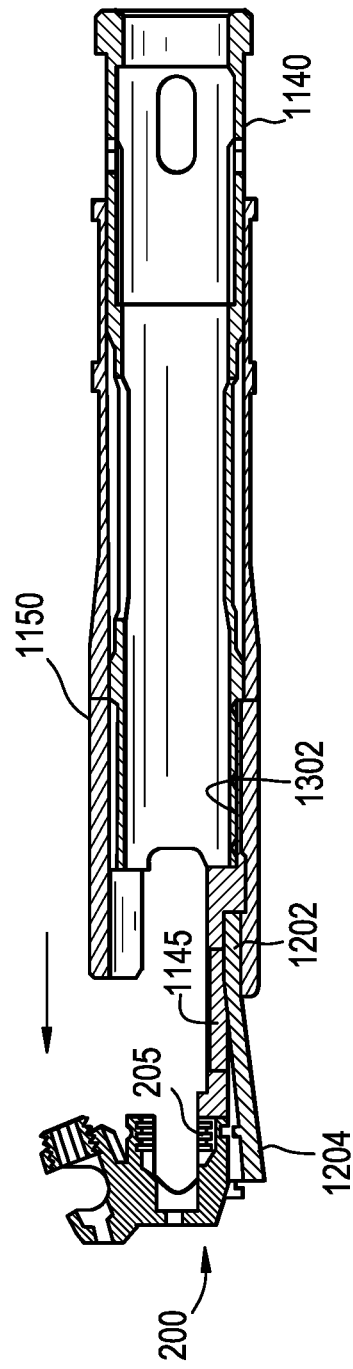
FIGS. 13A and 13B are schematic diagrams illustrating a locking operation of the unilateral locking mechanism according to the fourth embodiment.
Figure 13B:
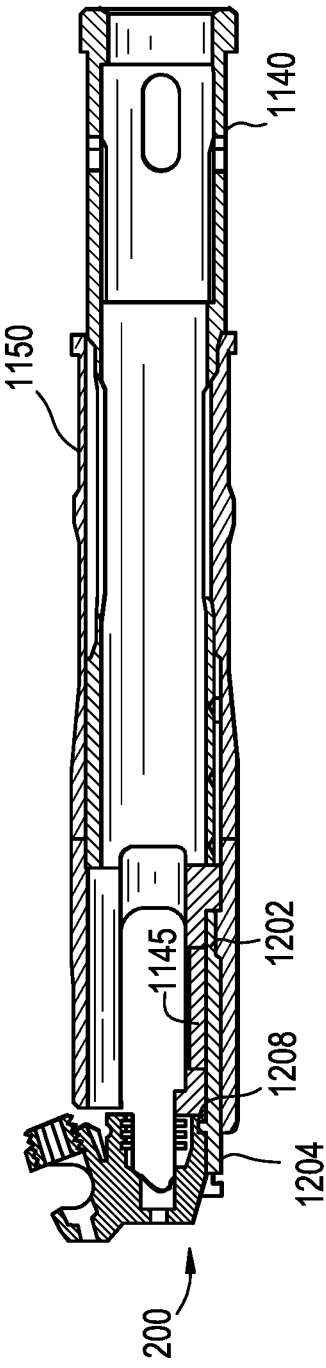

FIGS. 13A and 13B are schematic diagrams illustrating a locking operation of the unilateral locking mechanism according to the fourth embodiment. The locking sleeve 1150 may have a substantially tubular body having an inner diameter that is larger than an outer diameter of the tubular locking shaft 1140, thereby enabling the 1150 sleeve to slide longitudinally along the outer surface of the shaft 1140. As shown in FIG. 13A, the locking sleeve 1150 may be initially positioned in an unlocked or released configuration towards a proximal end of the locking shaft 1140. With the locking sleeve 1150 away from the free clasp head 1204, the free clasp head 1204 may be laterally biased to a resting position aligned outside the window 1210. In this unlocked configuration, the unilateral portion of an implant (e.g., 205) may be received into the pocket 302 formed in the partial tubular locking shaft 1145 as previously shown and described with reference to FIGS. 3A, 3B, 4A and 4B.

As shown in FIG. 13B, once the implant is positioned within the pocket, the locking sleeve 1150 may be moved distally to engage the free clasp head with a counterpart locking element formed in the unilateral portion of the implant 205, such as a groove or notch. For example, as the locking sleeve 1150 slides distally along the outer surface of the tubular locking shaft 1140, the inner surface 1203 and locking pin 1155 may slide along and exert a force against the proximal clasp portion 1202 towards the free clasp head 1204. As the sleeve 1150 reaches the free clasp head 1204, the force exerted on the free clasp head 1204 may urge the head into the window 1210, thereby enabling the lateral-facing surface protrusion 1208 on its face to engage a groove or notch formed in the unilateral portion of the implant (e.g., 205)

Figure 14A:
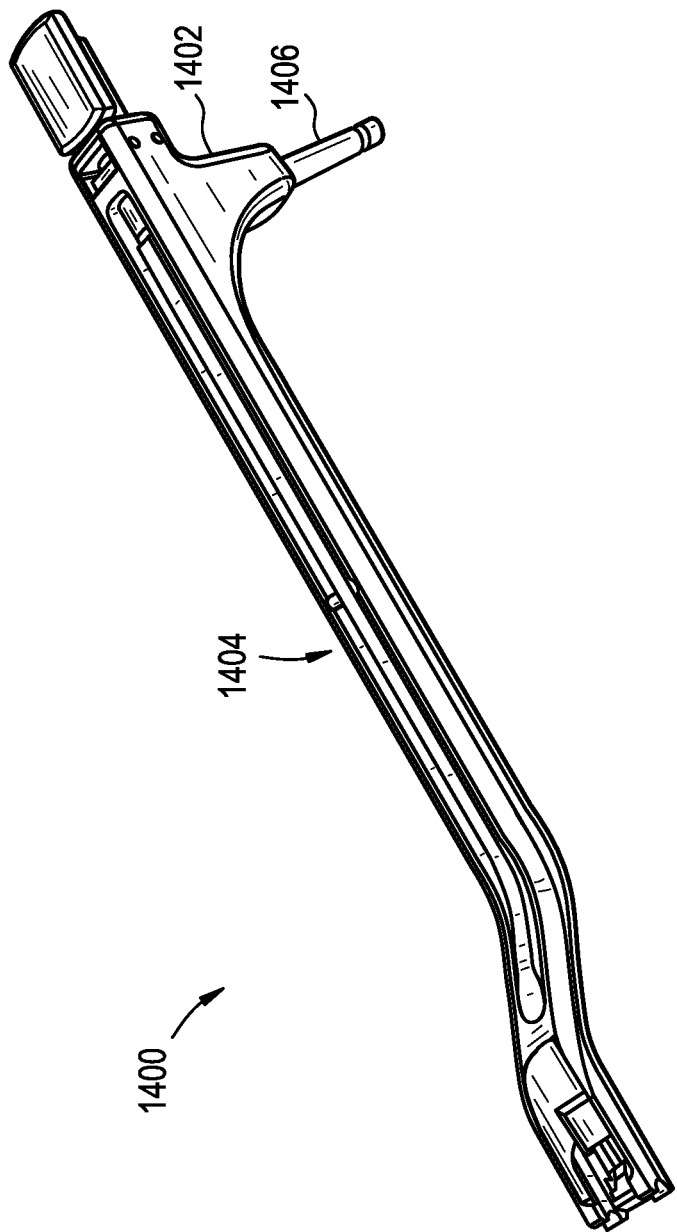

FIGS. 14A and 14B are schematic diagrams illustrating perspective and exploded views of a surgical instrument 1400 that includes a unilateral locking mechanism 1404 according to a fifth embodiment. As shown, the surgical instrument 1400 may include a proximal handle 1402 and a distal unilateral locking mechanism 1404. The handle 1402 may include a fixed attachment bar or shaft 1406 extending substantially perpendicular or obliquely to the handle 1402 and configured for attaching to a counter-torque lever (not shown). The locking mechanism 1404 may include an elongated body having a proximal end coupled to the handle 1402 and a distal end defining multiple locking elements configured to engage a unilateral portion of an implant.

The locking elements may be configured to engage the unilateral portion of an implant such that the locking elements are laterally offset from a proximal-distal axis of an open recess for receiving, e.g., a screw, nut and/or a rod. At least one of the locking elements may include a clasp 1410 extending from a distal end of a control shaft 1408. The control shaft 1408 may be configured to move in response to rotation of a knob 1418 or other type of actuation control, thereby causing the clasp 1410 to lock or unlock the implant. The control shaft 1408 may include a proximal shaft portion 1420 threadably coupled to a distal shaft portion 1422. As described in more detail below, the locking elements may be configured to contact, mate, interlock, or otherwise engage counterpart locking elements defined in a unilateral locking interface of an implant.

Figure 15:
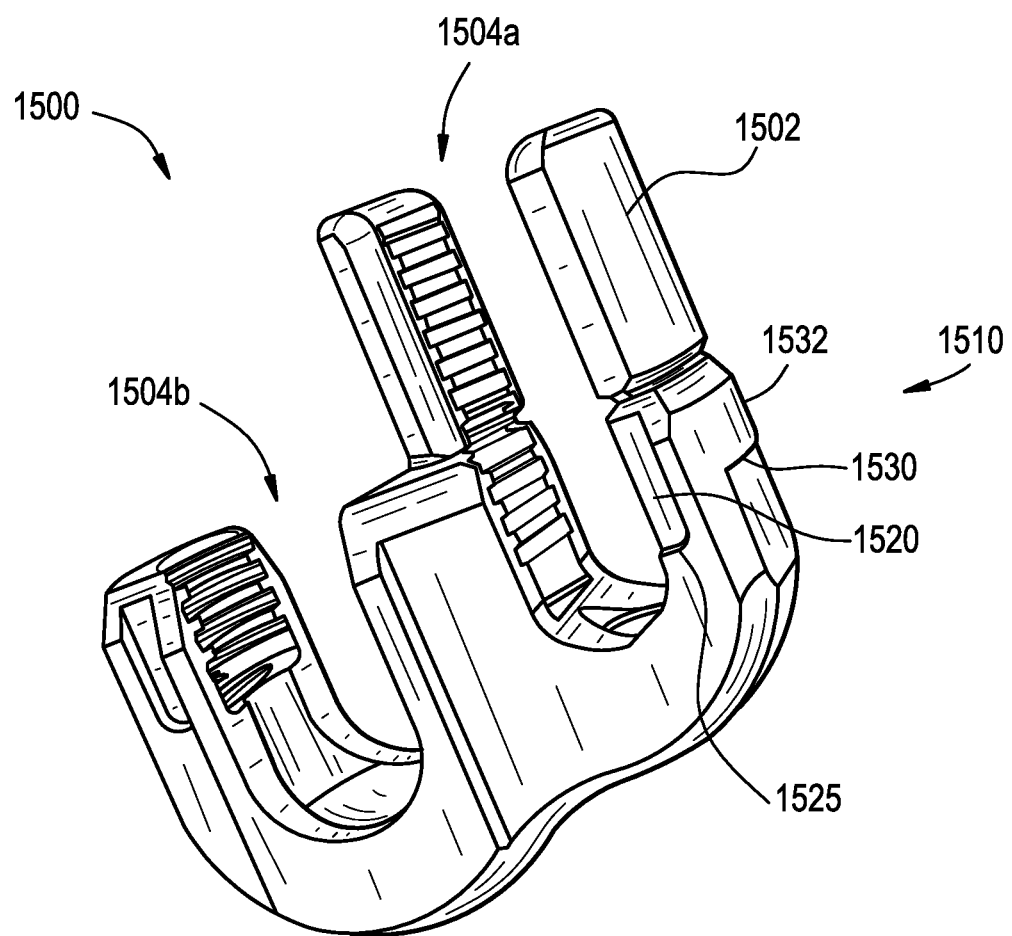
FIG. 15 is a schematic diagram illustrating various counterpart locking elements of a unilateral locking interface defined in a unilateral portion of an implant according to an embodiment.

FIG. 15 is a schematic diagram illustrating various counterpart locking elements of a unilateral locking interface defined in a unilateral portion of an implant 1500 according to an embodiment. Although the illustrated implant is a fixed U-U rod-to-rod connector 1500 having an extended reduction tab 1502, the counterpart unilateral locking interface may be integrated into other types of connectors and bone anchors. As shown, the implant 1500 may include one or more open recesses 1504a and 1504b (collectively 1504) formed in the body of the implant (e.g., for receiving a rod, nut, and/or a set screw). A unilateral portion of an implant may be a portion of the implant that is located towards one end of the implant. For example, the unilateral portion 1510 may correspond to an end portion of the implant 1500 opposing the open recesses 1504. As shown, the extended reduction tab 1502 may extend proximally from the unilateral portion 1510 of the implant. By defining the locking interface towards one side of the open recesses 1504, the recesses may continue to be accessible (e.g., not blocked) after the instrument's locking mechanism is engaged in a locked configuration.

As shown, the locking interface of the rod-to-rod connector 1500 may include a vertical groove or slot 1520 having a lateral-facing bearing surface formed in one or more of the sidewalls of the unilateral portion of the implant 1510 below the extended reduction tab 1502. The groove 1520 may also have a proximal-facing bearing surface formed on a distal edge 1525 of the groove or slot 1520. The grooves 1520 may intersect with the recess 1504a, as shown in FIG. 15, or may be spaced a distance apart from the recess. The locking interface of the implant may also include a distal-facing bearing surface 1530 formed on a lateral locking protrusion 1532 at the back surface of the implant and extending transversely between the pair of vertical grooves 1520. As discussed below, each of these counterpart locking elements may be configured to contact, mate, interlock, or otherwise engage the locking elements of the instrument's locking mechanism, thereby constraining movement of the implant in all directions.

Figure 16A:
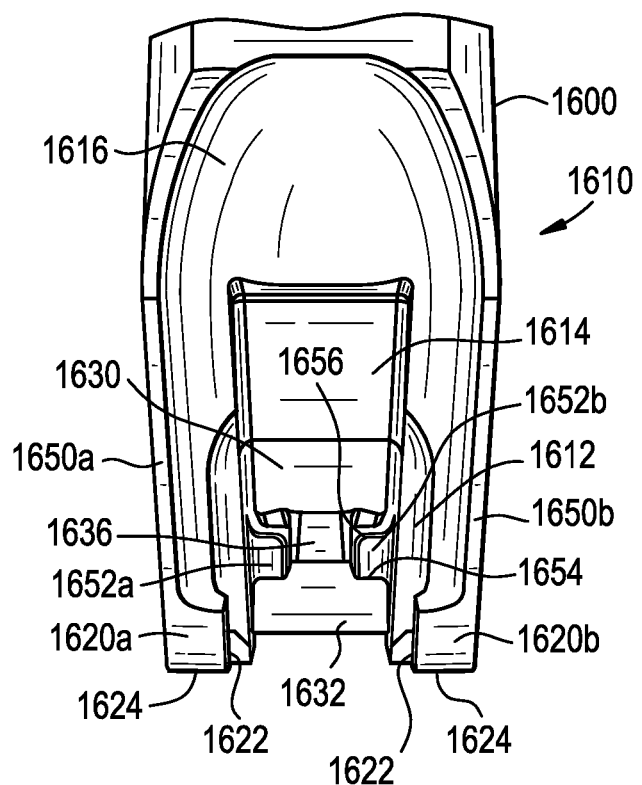
FIGS. 16A and 16B are schematic diagrams illustrating front and perspective views of the various locking elements at the distal end of the unilateral locking mechanism according to the fifth embodiment.
Figure 16B:
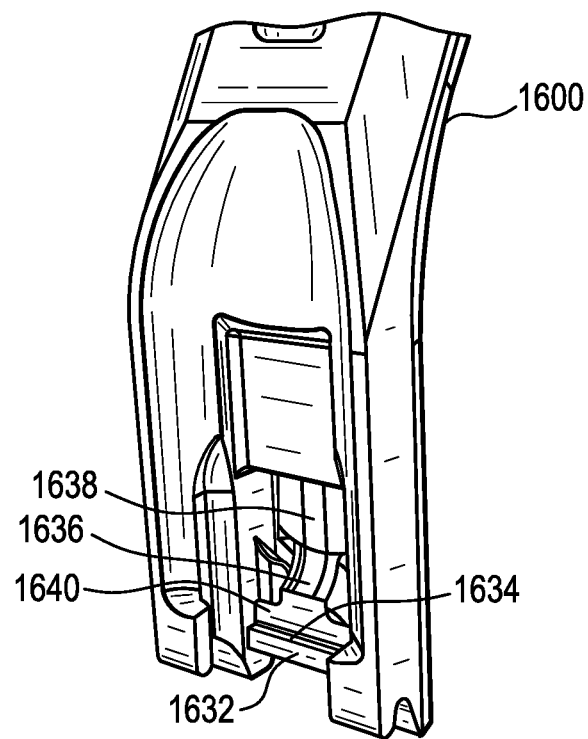

FIGS. 16A and 16B are schematic diagrams illustrating front and perspective views of the various locking elements at the distal end of the unilateral locking mechanism 1404 according to the fifth embodiment. As shown, the locking mechanism may include a pocket 1610 formed at the distal end of the elongated body 1600. The pocket 1610 may be configured to have a size and shape that accommodates a width and depth of a unilateral portion of an implant (e.g., 1510 of FIG. 15). For example, the pocket 1610 may include an implant-receiving pocket 1612 having a concave or other suitable shape that extends about or encompasses a unilateral end portion of a rod-to-rod connector (e.g., 1500) or other implant. The pocket 1610 may also include a tab-receiving pocket 1614 having a substantially rectangular or other suitable shape positioned above the implant-receiving pocket 1612 to accommodate a reduction tab extending proximally from the unilateral end portion of an implant. For example, the tab-receiving pocket 1614 may be a rectangular recess formed in the distal body 1600 above the implant-receiving pocket 1612 to accommodate the extended reduction tab 1502 of the fixed rod-to-rod connector 1500 of FIG. 15. The pocket 1610 may also include an instrument-receiving pocket 1616 having a size and shape configured to accommodate a distal head of an auxiliary instrument, such as a bell-shaped head of a nut driver. As shown, the pocket 1616 may have a substantially concave shape that expands distally towards the sidewalls of the body 1600 from a proximal tapered end of the pocket 1616. The implant-receiving pocket 1612 and the extended tab-receiving pocket 1614 may be formed as recesses in the inner surface of the instrument-receiving pocket 1616.

The locking mechanism may further include one or more prongs 1620a and 1620b (collectively or individually 1620) extending distally from the elongated body 1600. As shown, a pair of prongs 1620 may extend distally from a pair of arms 1650a and 1650b (collectively or individually 1650). Each prong 1620 may have a lateral-facing bearing surface 1622 and a distal-facing bearing surface 1624. The lateral-facing bearing surface 1622 of each prong 1620 may be configured to slide along a lateral-facing counterpart groove or slot formed in the sidewall of the unilateral portion of the implant (e.g. 1520 of FIG. 15), thereby constraining lateral movements of the implant (e.g., side-to-side and front-to-back movements). The distal-facing bearing surface 1624 of each prong 1620 may be configured to contact a proximal-facing bearing surface of a distal edge of the groove or slot (e.g., 1525 of FIG. 15), thereby constraining longitudinal movements of the implant in a proximal direction (e.g., upward movements). Although the use of the prongs 1620 may avoid the need for a stop beam having a distal-facing bearing surface previously described with reference to FIGS. 1A-13B for constraining proximal movements of an implant, other embodiments may include both prongs and stop beams for constraining proximal movements of an implant.

The locking mechanism may further include a retractable clasp 1630 disposed between the opposing faces of the spaced apart arms 1650 and through an opening at the back of the implant-receiving pocket 1612. The clasp 1630 may have a substantially rectangular body coupled at a proximal end to a control shaft (e.g., 1408 of FIG. 14B). The clasp 1630 may include a lateral locking protrusion 1632 having a proximal-facing bearing surface 1634.

The clasp 1630 may be configured to move upward and inward towards a locked configuration in which the clasp's proximal-facing bearing surface 1634 is forced against the distal-facing bearing surface of the implant's locking interface (e.g., 1530 of FIG. 15). The clasp 1630 may be further configured to move downward and outward away from the locked configuration towards an unlocked configuration in which the clasp's proximal-facing bearing surface 1634 is disengaged from the distal-facing bearing surface of the implant's locking interface.

As shown, the clasp 1630 may have a structure and operation similar to the clasp 610 shown and described with reference to FIGS. 6A through 7. For example, the clasp 1630 may include a narrow body region 1636 defined between a proximal end portion 1638 and a distal end portion 1640. The height, width and/or shape of the narrow body region 1636 may be configured to facilitate movement of the clasp between a pair of clasp guide structures 1652a and 1652b (collectively or individually 1652) protruding between opposing faces of the spaced apart arms 1650. Distal-facing bearing surfaces of the proximal end portion 1638 and proximal-facing bearing surfaces of the distal end portion 1640 may extend laterally from the narrow body region 1636 and be configured to slide against the clasp guide structures 1652 to guide the clasp 1630 in and out of a locked configuration with the implant. For example, the clasp guide structures 1652 may each have a cross-sectional shape of a rhombus or other parallelogram oriented to form distal-facing ramped bearing surfaces 1654 and proximal-facing ramped bearing surfaces 1656. The distal-facing ramped bearing surfaces 1654 may be obliquely angled to guide the clasp 1630 upward and inward towards the locked configuration in response to proximal movements of the control shaft. The proximal-facing ramped bearing surfaces 1656 may be obliquely angled to guide the clasp 1630 downward and outward away from the locked configuration in response to distal movements of the control shaft. Alternatively, the clasp 1630 may be configured to have a structure and operation similar to the structure and operation of any of the embodiments shown and described with reference to FIGS. 1A-13B.

FIGS. 17A and 17B are schematic diagrams illustrating a locking operation between the unilateral locking mechanism according to the fifth embodiment. As shown in FIG. 17A, the distal end of the locking mechanism 1600 may be initially positioned over a proximal end of an implant 1500 such that the implant-receiving pocket 1612 may be aligned with the unilateral portion of the implant 1510. As the locking mechanism 1600 is inserted distally towards the implant 1500, the extended reduction tab 1502 of the implant 1500 may be received in the tab-receiving pocket 1614. As insertion of the locking mechanism 1600 continues, the prongs 1620 of the locking mechanism may slide longitudinally along the lateral-facing grooves or slots 1520 of the implant's locking interface, thereby guiding the unilateral portion 1510 of the implant 1500 proximally into the implant-receiving pocket 1612. As shown in FIG. 17B, the prongs 1620 may continue to slide along the grooves until the distal-facing bearing surface 1624 of the prongs 1620 contacts or abuts the proximal-facing bearing surface at the distal edge 1525 of the groove 1520. In response to the prongs 1620 of the locking mechanism contacting the distal edge 1525 of the implant's lateral-facing groove or slot 1520, further movement of the implant in the lateral and proximal directions is prevented. The clasp 1630 may be engaged to lock the implant in place as previously described with reference to FIG. 7 in order to prevent movement of the implant in the distal direction.

Figure 18A:
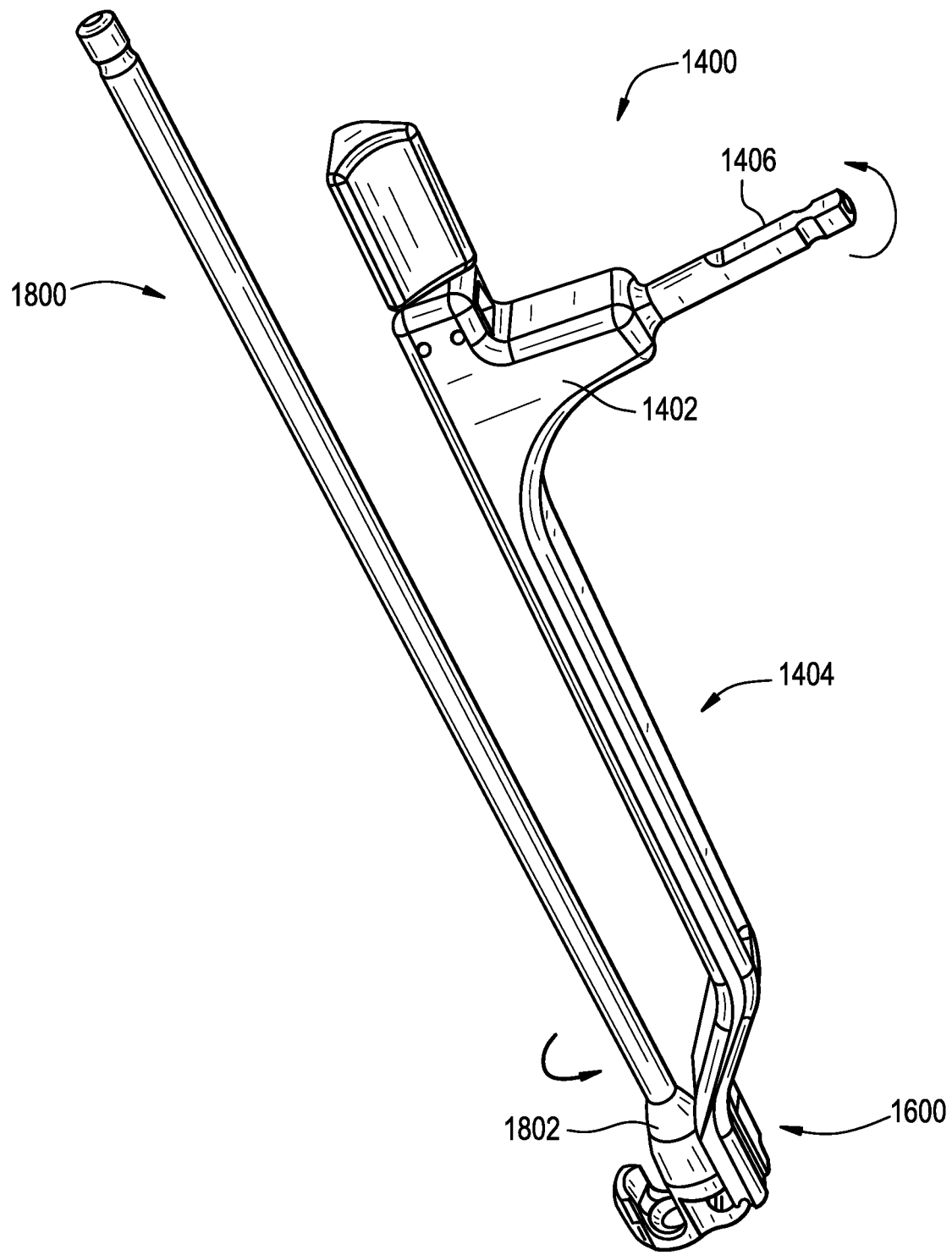
FIGS. 18A and 18B are schematic diagrams illustrating a surgical procedure that may be performed using the surgical instrument according to the fifth embodiment.
Figure 18B:
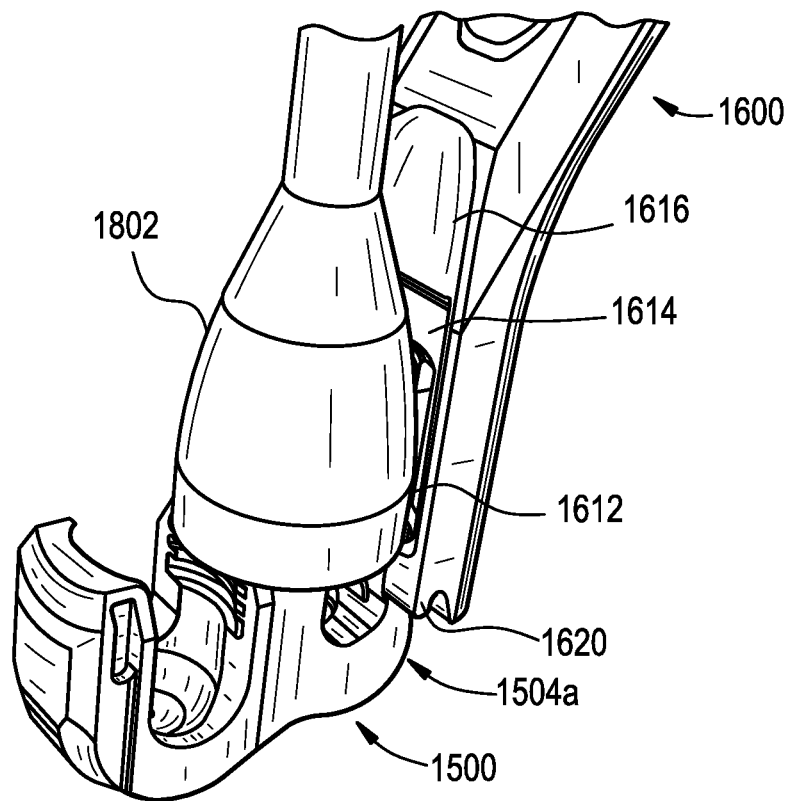

FIGS. 18A and 18B are schematic diagrams illustrating a surgical procedure that may be performed using the surgical instrument according to the fifth embodiment. In particular, the surgical instrument 1400 may be used to rigidly hold a rod-to-rod connector 1500 in place while concurrently performing a surgical procedure using an auxiliary instrument, such as a driver instrument 1800. For example, the driver instrument 1800 may be used to tighten a locking nut or screw to the connector 1500. To enable the driver instrument 1800 with direct access to the connector 1500, the elongated body of the locking mechanism 1404 may include one or more angled body segments configured to laterally offset the handle portion 1402 away from a proximal-distal axis of the connector 1500. While holding onto the handle portion 1402 of the surgical instrument 1400, a surgeon can position the distal head 1802 of a driver instrument 1800 directly into engagement with the connector 1500 or a locking nut or screw thereof. To tighten a nut and/or screw to the connector 1500, the driver instrument 1800 applies a torqueing force. To maintain the position of the connector 1500 while applying the torqueing force to the nut and/or screw, a counter-torque lever (not shown) may be attached to a fixed attachment bar or shaft 1406 extending substantially perpendicular or obliquely to the handle 1402. The fixed attachment bar or shaft 1406 may include various coupling structures for connecting the counter-torque lever to the handle 1402. The counter-torque lever may be any type of lever or handle known to one of ordinary skill in the art that can enable the surgeon to manually apply a counter-torqueing force opposite and substantially equal to the torqueing force applied using the driver instrument 1800. For example, when the driver instrument 1800 is used to apply a clockwise torqueing force to the nut and/or screw, the surgeon may use the counter-torque lever attached to the fixed attachment bar or shaft 1406 to apply a counter-clockwise torqueing force to prevent the surgical instrument 1400, and thus the connector 1500, from twisting.

FIG. 18B further illustrates the distal end of the locking mechanism 1600 having an instrument-receiving pocket 1616 that accommodates the size and shape of the distal head 1802 of the driver instrument 1800, such that the distal head may freely rotate within the pocket 1616 while applying a torque to drive the nut and/or screw through the connector 1500. As shown, the pocket 1616 may have a substantially concave shape that expands distally towards the sidewalls of the body 1600 from a proximal tapered end of the pocket 1616. The implant-receiving pocket 1612 and the extended tab-receiving pocket 1614 may be formed as recesses in the inner surface of the instrument-receiving pocket 1616.

Figure 19A:
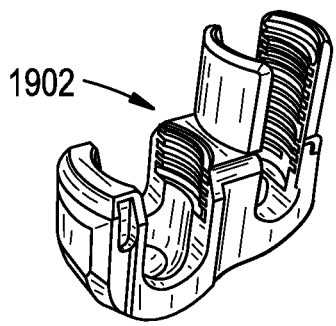
FIG. 19A through 19G are schematic diagrams of various implants to which the various embodiments may be applied.
Figure 19B:
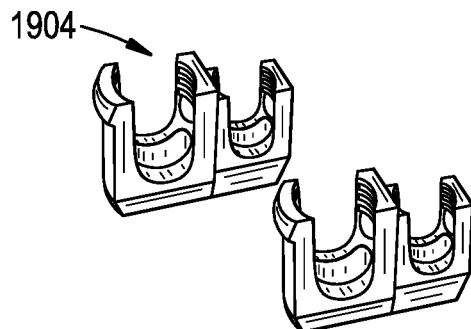
Figure 19C:
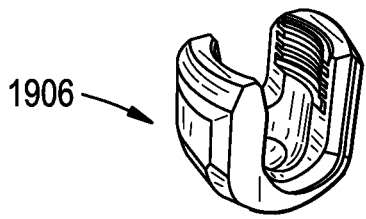
Figure 19D:
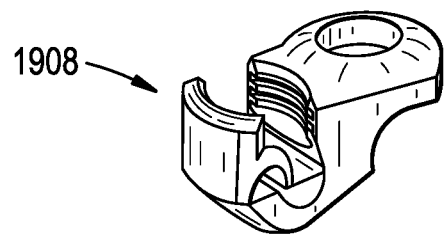
Figure 19E:
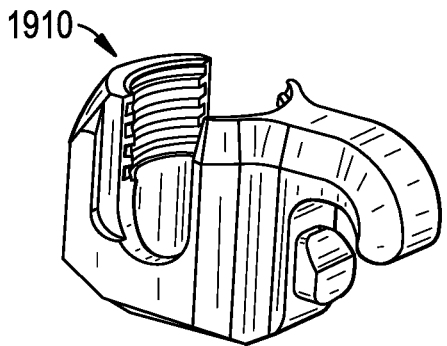
Figure 19F:
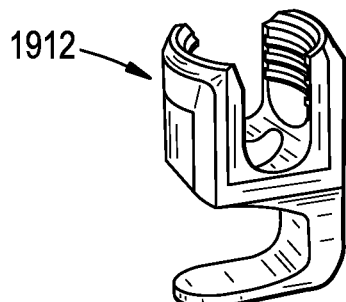
Figure 19G:
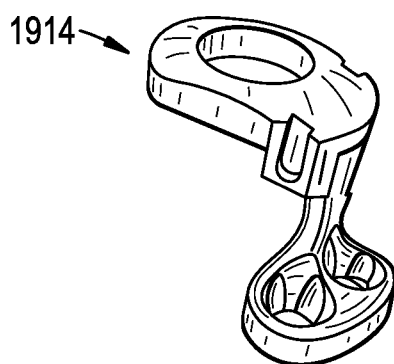

FIG. 19A through 19G are schematic diagrams of various implants to which the various embodiments may be applied. For example, the various embodiments of the instruments configured with a unilateral locking mechanism (e.g., instruments 100, 600, 800, 1100 and 1400) may be used to rigidly hold onto a unilateral portion of various types and configurations of bone anchors and/or connectors, such as without limitation a fixed rod-to-rod connector 1902, an articulating rod-to-rod connector 1904, a receiver head 1906 of a bone anchor, e.g., of a polyaxial bone screw, a rod-to-anchor connector 1908, a side or bottom loading rod-to-rod connector 1910, a bone or lamina hook 1912, a multipoint implant 1914, cross-connector adapters, open connectors, closed connectors, and so forth. Implants can include multiple counterpart locking elements or multiple sets of counterpart locking elements. For example, an implant having multiple arms, e.g., first and second opposed arms, can include a counterpart locking geometry (e.g., a set of counterpart locking elements) formed in any one or more of said arms. This can advantageously allow unilateral implant holders of the type described herein to be interchangeably attached to any one or more arms of the implant. FIG. 19F shows an exemplary implant having counterpart locking elements on each of first and second opposed arms of the implant. In some embodiments, the vertical groove locking elements of the implant can be open to or can intersect with a rod-slot of the implant, for example as shown in FIGS. 19C, 19D, 19E, and 19F. In some embodiments, the vertical groove locking elements of the implant can be separate from and spaced a distance apart from a rod-slot of the implant, for example as shown in FIGS. 19A and 19B.

Exemplary implants in which counterpart locking elements for use with the instruments described herein can be incorporated are disclosed in U.S. application Ser. No. 15/073,020 filed on Mar. 17, 2016 and entitled "MULTI-POINT FIXATION IMPLANTS" (now issued as U.S. Pat. No. 9,962,192); U.S. application Ser. No. 15/158,127 filed on May 18, 2016 and entitled "IMPLANT CONNECTORS AND RELATED METHODS" (now issued as U.S. Pat. No. 10,517,647); U.S. application Ser. No. 15/284,587 filed on Oct. 4, 2016 and entitled "IMPLANT CONNECTORS AND RELATED METHODS" (now issued as U.S. Pat. No. 10,321,939); U.S. application Ser. No. 15/377,449 filed on Dec. 13, 2016 and entitled "IMPLANT ADAPTERS AND RELATED METHODS" (now issued as U.S. Pat. No. 10,398,476); U.S. application Ser. No. 15/471,075 filed on Mar. 28, 2017 and entitled "ARTICULATING IMPLANT CONNECTORS AND RELATED METHODS" (now issued as U.S. Pat. No. 10,561,454); U.S. application Ser. No. 15/430,188 filed on Feb. 10, 2017 and entitled "TANDEM ROD CONNECTORS AND RELATED METHODS" (now issued as U.S. Pat. No. 10,238,432); and U.S. application Ser. No. 15/208,872 filed on Jul. 13, 2016 and entitled "BONE ANCHOR ASSEMBLIES AND RELATED INSTRUMENTATION" (now issued as U.S. Pat. No. 10,463,402): each of which is hereby incorporated by reference herein.

While the instruments and methods illustrated and described herein generally involve attaching to spinal implant hardware, it will be appreciated that the instruments and methods herein can be used with various other types of fixation or stabilization hardware, in any bone, in non-bone tissue, or in non-living or non-tissue objects. The implants disclosed herein can be fully implanted, or can be used as part of an external fixation or stabilization system. The devices and methods disclosed herein can be used in minimally-invasive surgery and/or open surgery.

The devices disclosed herein and the various component parts thereof can be constructed from any of a variety of known materials. Exemplary materials include those which are suitable for use in surgical applications, including metals such as stainless steel, titanium, or alloys thereof, polymers such as PEEK, ceramics, carbon fiber, and so forth. The various components of the devices disclosed herein can be rigid or flexible. One or more components or portions of the device can be formed from a radiopaque material to facilitate visualization under fluoroscopy and other imaging techniques, or from a radiolucent material so as not to interfere with visualization of other structures. Exemplary radiolucent materials include carbon fiber and high-strength polymers.

The preceding description of the disclosed embodiments is provided to enable any person skilled in the art to make or use what is described. Various modifications to these embodiments will be readily apparent to those skilled in the art, and the generic principles defined herein may be applied to other embodiments without departing from the scope of the present disclosure. Thus, the present disclosure is not intended to be limited to the embodiments shown herein but is to be accorded the widest scope consistent with the principles and features disclosed herein.

What is claimed is:

1. A method of securing an implant to a surgical instrument, comprising:
    aligning a unilateral locking mechanism of the surgical instrument with a unilateral portion of the implant;
    inserting the unilateral locking mechanism onto the unilateral portion of the implant until a distal-facing bearing surface of the unilateral locking mechanism engages a counterpart proximal-facing bearing surface of the unilateral portion of the implant; and
    controlling longitudinal movement of a clasp of the unilateral locking mechanism such that a proximal-facing bearing surface of the clasp engages a counterpart distal-facing bearing surface of the unilateral portion of the implant.

2. The method of claim 1 wherein inserting the unilateral locking mechanism onto the unilateral portion of the implant comprises sliding at least a pair of lateral-facing bearing surfaces along at least a pair of lateral-facing grooves defined along the unilateral portion of the implant.

3. The method of claim 1 wherein controlling the movement of the clasp comprises actuating a control shaft coupled to the clasp such that movements of the control shaft in a first direction cause a proximal-facing bearing surface of the clasp to engage a counterpart distal-facing bearing surface of the unilateral portion of the implant.

4. The method of claim 3, wherein a pin and slot interface is defined between the control shaft and an elongate body of the unilateral locking mechanism; and
    actuating the control shaft coupled to the clasp in the first direction causes the pin to move along the slot and guide movement of the clasp.

5. The method of claim 3, wherein the unilateral locking mechanism defines a pair of spaced apart arms forming an implant-receiving pocket therebetween, the unilateral locking mechanism including a pair of clasp guide structures protruding between opposing faces of the pair of spaced apart arms; and
    wherein the pair of clasp guide structures urge the clasp upward and inward towards a locked configuration when the control shaft is actuated in the first direction.

6. The method of claim 1 wherein controlling the movement of the clasp comprises sliding a locking sleeve over an outer portion of the clasp such that a surface protrusion formed on an inner portion of the clasp engages a counterpart groove formed in the unilateral portion of the implant.

7. The method of claim 1, further comprising:
    inserting a rod into the implant while the implant is secured to the instrument.

8. The method of claim 1 wherein the distal-facing bearing surface of the unilateral locking mechanism comprises a distal-facing bearing surface formed on one or more prongs extending from a distal end of the unilateral locking mechanism and wherein inserting the unilateral locking mechanism onto the unilateral portion of the implant comprises sliding the one or more prongs along one or more lateral-facing grooves defined along the unilateral portion of the implant until the distal-facing surface of the one or more prongs contacts a distal edge of the one or more lateral-facing grooves.

9. The method of claim 1, wherein aligning the unilateral locking mechanism of the surgical instrument with the unilateral portion of the implant further comprises positioning the surgical instrument over a proximal end of the implant such that an implant-receiving pocket of the unilateral locking mechanism is aligned with the unilateral portion of the implant.

10. The method of claim 9, wherein inserting the unilateral locking mechanism onto the unilateral portion of the implant further comprises moving the unilateral locking mechanism relative to the implant such that the implant-receiving pocket of the unilateral locking mechanism receives at least a portion of the unilateral portion of the implant.

11. The method of claim 10, wherein the implant includes a reduction tab extending proximally from the unilateral portion of the implant and the unilateral locking mechanism includes a tab-receiving pocket formed proximally of the implant-receiving pocket; and
    wherein inserting the unilateral locking mechanism onto the unilateral portion of the implant further comprises moving the unilateral locking mechanism relative to the implant such that the tab-receiving pocket of the unilateral locking mechanism receives at least a portion of the reduction tab of the implant.

12. The method of claim 9, wherein controlling movement of the clasp of the unilateral locking mechanism such that the bearing surface of the clasp engages the counterpart bearing surface of the unilateral portion of the implant comprises moving the bearing surface radially inward through an opening in the implant-receiving pocket.

13. The method of claim 1, wherein the distal-facing bearing surface of the unilateral locking mechanism is formed on a stop beam located proximal to a distal end of the unilateral locking mechanism.

14. The method of claim 1, wherein the implant includes at least one recess configured to receive a fixation element; and
    wherein the clasp engages the counterpart bearing surface of the unilateral portion of the implant such that the at least one recess of the implant is unobstructed by the surgical instrument.

15. The method of claim 1, wherein the clasp engages the counterpart bearing surface of the unilateral portion of the implant such that a central longitudinal axis of the surgical instrument is non-coaxial with a central longitudinal axis of the implant.

16. The method of claim 1, wherein the bearing surface of the clasp engages the counterpart bearing surface of the unilateral portion of the implant thereby constraining longitudinal movement of the implant in a distal direction.

17. The method of claim 1, wherein a body of the unilateral locking mechanism defines a pair of spaced apart arms forming an implant-receiving pocket therebetween.

18. The method of claim 17, wherein controlling the movement of the clasp of the unilateral locking mechanism such that the bearing surface of the clasp engages the counterpart bearing surface of the unilateral portion of the implant comprises moving the clasp radially-inward relative to the pair of spaced apart arms.

19. The method of claim 1, further comprising tightening a locking mechanism within a recess of the implant while the clasp of the unilateral locking mechanism engages the counterpart bearing surface of the unilateral portion of the implant.

20. A method of securing an implant to a surgical instrument, comprising:
   aligning a unilateral locking mechanism of the surgical instrument with a unilateral portion of the implant;
   inserting the unilateral locking mechanism onto the unilateral portion of the implant until a distal-facing bearing surface of the unilateral locking mechanism engages a counterpart proximal-facing bearing surface of the unilateral portion of the implant;
   wherein inserting the unilateral locking mechanism onto the unilateral portion of the implant comprises sliding at least a pair of lateral-facing bearing surfaces along at least a pair of lateral-facing grooves defined along the unilateral portion of the implant; and
   controlling movement of a clasp of the unilateral locking mechanism such that a bearing surface of the clasp engages a counterpart bearing surface of the unilateral portion of the implant.

21. A method of securing an implant to a surgical instrument, comprising:
   aligning a unilateral locking mechanism of the surgical instrument with a unilateral portion of the implant;
   inserting the unilateral locking mechanism onto the unilateral portion of the implant until a distal-facing bearing surface of the unilateral locking mechanism engages a counterpart proximal-facing bearing surface of the unilateral portion of the implant; and
   controlling movement of a clasp of the unilateral locking mechanism such that a bearing surface of the clasp engages a counterpart bearing surface of the unilateral portion of the implant,
   wherein the distal-facing bearing surface of the unilateral locking mechanism comprises a distal-facing bearing surface formed on one or more prongs extending from a distal end of the unilateral locking mechanism and wherein inserting the unilateral locking mechanism onto the unilateral portion of the implant comprises sliding the one or more prongs along one or more lateral-facing grooves defined along the unilateral portion of the implant until the distal-facing surface of the one or more prongs contacts a distal edge of the one or more lateral-facing grooves.

22. A method of securing an implant to a surgical instrument, comprising:
   aligning a unilateral locking mechanism of the surgical instrument with a unilateral portion of the implant;
   inserting the unilateral locking mechanism onto the unilateral portion of the implant until a distal-facing bearing surface of the unilateral locking mechanism engages a counterpart proximal-facing bearing surface of the unilateral portion of the implant;
   wherein inserting the unilateral locking mechanism onto the unilateral portion of the implant further comprises moving the unilateral locking mechanism relative to the implant such that the implant-receiving pocket of the unilateral locking mechanism receives at least a portion of the unilateral portion of the implant; and
   controlling movement of a clasp of the unilateral locking mechanism such that a bearing surface of the clasp engages a counterpart bearing surface of the unilateral portion of the implant,
   wherein the implant includes a reduction tab extending proximally from the unilateral portion of the implant and the unilateral locking mechanism includes a tab-receiving pocket formed proximally of the implant-receiving pocket; and
   wherein inserting the unilateral locking mechanism onto the unilateral portion of the implant further comprises moving the unilateral locking mechanism relative to the implant such that the tab-receiving pocket of the unilateral locking mechanism receives at least a portion of the reduction tab of the implant.

23. A method of securing an implant to a surgical instrument, comprising:
   aligning a unilateral locking mechanism of the surgical instrument with a unilateral portion of the implant;
   inserting the unilateral locking mechanism onto the unilateral portion of the implant until a distal-facing bearing surface of the unilateral locking mechanism engages a counterpart proximal-facing bearing surface of the unilateral portion of the implant; and
   controlling movement of a clasp of the unilateral locking mechanism such that a bearing surface of the clasp engages a counterpart bearing surface of the unilateral portion of the implant,
   wherein the clasp engages the counterpart bearing surface of the unilateral portion of the implant such that a central longitudinal axis of the surgical instrument is non-coaxial with a central longitudinal axis of the implant.

* * * * *